(12) United States Patent
Chalana et al.

(10) Patent No.: US 7,041,059 B2
(45) Date of Patent: *May 9, 2006

(54) 3D ULTRASOUND-BASED INSTRUMENT FOR NON-INVASIVE MEASUREMENT OF AMNIOTIC FLUID VOLUME

(75) Inventors: Vikram Chalana, Mill Creek, WA (US); Stephen Dudycha, Bothell, WA (US); Gerald McMorrow, Kirkland, WA (US)

(73) Assignee: Diagnostic Ultrasound Corporation, Woodinville, WA (US)

( * ) Notice: Subject to any disclaimer, the term of this patent is extended or adjusted under 35 U.S.C. 154(b) by 174 days.

This patent is subject to a terminal disclaimer.

(21) Appl. No.: 10/443,126

(22) Filed: May 20, 2003

(65) Prior Publication Data
US 2004/0024302 A1 Feb. 5, 2004

Related U.S. Application Data

(60) Provisional application No. 60/423,881, filed on Nov. 5, 2002, provisional application No. 60/400,624, filed on Aug. 2, 2002.

(51) Int. Cl.
*A61B 8/00* (2006.01)

(52) U.S. Cl. .................. 600/437; 600/443; 600/449

(58) Field of Classification Search ........ 600/437–472; 73/625, 626; 367/7, 11, 130; 128/916
See application file for complete search history.

(56) References Cited

U.S. PATENT DOCUMENTS

| | | | |
|---|---|---|---|
| 5,235,985 A | 8/1993 | McMorrow et al. | |
| 5,588,435 A | 12/1996 | Weng et al. | |
| 5,605,155 A | 2/1997 | Chalana et al. | |
| 5,644,513 A | 7/1997 | Rudin et al. | |
| 6,213,949 B1 | 4/2001 | Ganguly et al. | |
| 6,346,124 B1 | 2/2002 | Geiser et al. | |
| 6,375,616 B1 | 4/2002 | Soferman et al. | |
| 6,610,013 B1 | 8/2003 | Fenster et al. | |
| 6,695,780 B1 | 2/2004 | Nahum et al. | |
| 2002/0133075 A1 | 9/2002 | Abdelhak | |
| 2003/0174872 A1 | 9/2003 | Chalana et al. | |

OTHER PUBLICATIONS

E.F. Magann et al., Utlrasound estimation of Amniotic Fluid Volume Using the Largest Vertical Pocket Containing Umbilical Cord: Measure to or Through the Cord?, Ultrasound Obstet Gynecol 2002; 20: 464-467.

(Continued)

*Primary Examiner*—Ali Imam
(74) *Attorney, Agent, or Firm*—Black Lowe & Graham PLLC

(57) ABSTRACT

A hand-held 3D ultrasound instrument is disclosed which is used to non-invasively and automatically measure amniotic fluid volume in the uterus requiring a minimum of operator intervention. Using a 2D image-processing algorithm, the instrument gives automatic feedback to the user about where to acquire the 3D image set. The user acquires one or more 3D data sets covering all of the amniotic fluid in the uterus and this data is then processed using an optimized 3D algorithm to output the total amniotic fluid volume corrected for any fetal head brain volume contributions.

34 Claims, 15 Drawing Sheets

OTHER PUBLICATIONS

Gramellini et al., Sonographic Assessment of Amniotic Fluid Volume Between 11 and 24 Weeks of Gestation: Construction of Reference intervals Related to Gestational Age, Ultrasound Obstet Gvnecol 2001: 17: 410-415.

Mann et al., Novel Technique for Assessing Amniotic Fluid Volume Use of a Three-Dimensional Bladder Scanner, The journal of Maternal-Fetal Medicine 9:308-310 (2000).

Grover et al., Three-Dimensional Method for Determination of Amniotic Fluid Volume in Intrauterine Pockets, Obstetrics and Gynecology 1997; 90, No. 6: 1007-1010.

Cheng et al., Boundary Extraction Method for Three Dimensional Ultrasonic Echo Imaging Using Fuzzy and Relaxation Techniques, TNE 1993 IEEE, Nuclear Science Symposium: Medical Imaging Oct. 30-Nov. 6, 1993: PT 3, 1610-1614.

Ross, Michael G., Am J. Obstet Gynecol Aug. 1993: vol. 169, No. 2: 435-437.

Sagiv C., et al., "Application of a Semiautomatic Boundary Detection Algorithm for the Assessment of Amniotic Fluid Quantity from Ultrasound Images," Ultrasound in Medicine & Biology, 1999, vol. 25, No. 4, pp. 515-526.

Birnholz et al., "Amniotic Fluid Accumulation in the First Trimester," *J. Ultrasound Med.,* 4:597-602 (1995); American Institute of Ultrasound in Medicine, Illinois.

Ohashi et al., "Boundary Estimation for Ultrasonic 3-D Imaging," *Spie,* 1898:480-486 (1993); *Image Processing,* Keio University, Japan.

Grover et al., "Three-Dimensional Amniotic Fluid Volume," *Obstetrics & Gynecology* (Dec. 1997) 1007-1010, 90:6; Elsevier Science, Inc., University of California Los Angeles.

Mann et al., "Novel Technique for Assessing Amniotic Fluid Volume: Use of a Three-Dimensional Bladder Scanner," *J. of Maternal Fetal Med.* (2000) 9:308-310, Torrance, California.

Ross, "Amniotic Fluid Volume Determination," *Letter to the Editor,* 169 (2:1), *Am. J. Obstet. Gynecol.,* Aug. 1993.

Cheng et al., "Boundary Extraction Method for Three Dimesional Ultrasonic Echo Imaging Using Fuzzy Reasoning and Relaxation Techniques," (1994) 1610-1614 IEEE, Tokyo, Japan.

Rutherford et al., "The Four-Quadrant Assessment of Amniotic Fluid Volume: An Adjunct to Antepartum Fetal Heart Rate Testing," (1987) 353-356 70:3 (Part 1) *Obstetrics & Gynecology.*

Chamberlain et al., "Ultrasound Evaluation of Amniotic Fluid Vol.; II. The Relationship of Increased Amniotic Fluid vol. to Perinatal Outcome," (Oct. 1, 1984) 250-254 *Am. J. Ob. Gyn.,* Canada.

Phelan et al., "Amniotic Fluid Volume Assessment with the Four-Quadrant Technique at 36-42 Weeks' Gestation," (Jul. 1987) 540-42, 32:7 Dept. Ob. Gyn., UCLA, California.

Chamberlain, Paul, "Amniotic Fluid Volume: Ultrasound Assessment and Clinical Significance," (Oct. 1985) 163-167, Seminars in Perinatology 9:4, Grune & Stratton, Inc., Galway, Ireland.

Crowley et al., "The Value of Ultrasound Measurement of Amniotic Fluid Volume In The Management of Prolonged Pregnancies," (May 1984) 444-448 vol. 91, British Journal of Obstetrics and Gynaecology.

Stangenberg et al., "Amniotic Fluid Volumes In Pregnant Diabetics During the Last Trimester: A Comparative Study Using Ultrasound and PAH Dilution," *Acta Obstet Gynecol Scand* (1982) 61:313-316, Stockholm, Sweden.

Manning et al., "Qualitative Amniotic Fluid Volume Determination By Ultrasound: Antepartum Detection of Intrauterine Growth Retardation," Thirty-Sixth Annual Meeting of The Society of Obstetricians and Gynaecologists of Canada, Jasper, Alberta, Canada, Jun. 10-14, 1980. (Feb. 1, 1981), 254-258, *Am. J. Obstet. Gynecol.,* C.V. Mosby Co., Canada.

Weissman et al., "Sonographic Measurement of Amniotic Fluid Volume in the First Trimester of Pregnancy," (Jun. 23, 1996) American Institute of Ultrasound in Medicine, *J Ultrasound Med.,* 15:771-774.

Sagiv et al, "Application of a Semiautomatic Boundary Detection Algorithm for the Assessment of Amniotic Fluid Quantity from Ultrasound Images," (1999) *Ultrasound in Med. & Biol.,* 25:4 515-526 *World Federation for Ultrasound in Medicine,* Elsevier Science, Inc., Tel Aviv Unversity, Israel.

Magann et al., "Measurement of Amniotic Fluid Volume: Accuracy of Ultrasonography Techniques," (Dec. 1992) 1533-1537, *Am. J. Obstet. Gynecol.,* Jackson, Mississippi, and Augusta, Georgia.

Myles et al., "Four-Quadrant Assessment of Amniotic Fluid Volume: Distribution's Role in Predicting Fetal Outcome," (1992) 769-774, 80:5, *Ob. & Gyn.,* The American College of Obstetricians and Gynecologists.

Moore, MD, Thomas R., "Superiority of the Four-Quadrant Sum Over the Single-Deepest-Pocket Technique in Ultrasonographic Identification of Abnormal Amniotic Fluid Vols.," 762-767, 163:3, U. of California, San Diego.

Jeng et al., "Amniotic Fluid Index Measurement with the Four-Quadrant Technique During Pregnancy," (1990) 35:7, 674-677, *J. Reproductive Medicine,* The Journal of Reproductive Medicine, Inc.

Schiff et al., "Standardized Measurement of Amniotic Fluid Volume by Correlation of Sonography With Dye Dilution Technique," (1990) 44-46, 76:1 Department of Obstetrics and Gynecology; Tel Aviv, Israel.

Gramellini et al., "Sonographic Assessment of Amniotic Fluid Volume Between 11 and 24 Weeks of Gestation: Construction of Reference Intervals Related to Gestational Age," (2001) *Ultrasound Obstet. Gynecol.,* 17:410-415, Parma, Italy.

Magann et al., "Ultrasound Estimation of Amniotic Fluid Volume Using the Largest Vertical Pocket Containing Umbilical Cord: Measure To or Through Cord?," (2002) *Ultrasound Obstet. Gynecol.,* 20:464-467; Australia, Mississippi and South Carolina.

Magann et al., "Ultrasound Estimate of Amniotic Fluid Volume: Color Doppler Overdiagnosis of Oligohydraminos," (2001) 98:1, 71-74, *Obstetrics & Gynecology,* Elsevier Science, Inc., South Carolina and Mississippi.

Schrimmer et al., "Sonographic Evaluation of Amniotic Fluid Volume," (2002) 45:4, 1026-1038, *Clinical Obstetrics and Gynecology,* Lippincott Williams & Wilkins, Inc., University of California, San Diego.

Sahin et al., "Estimation of the Amniotic Fluid Volume Using the Cavalieri Method on Ultrasound Images," (2003) 82:25-30, *Int'l. J. of Gynecol. And Obstet.,* Elsevier Science, Inc., Samsun, Turkey.

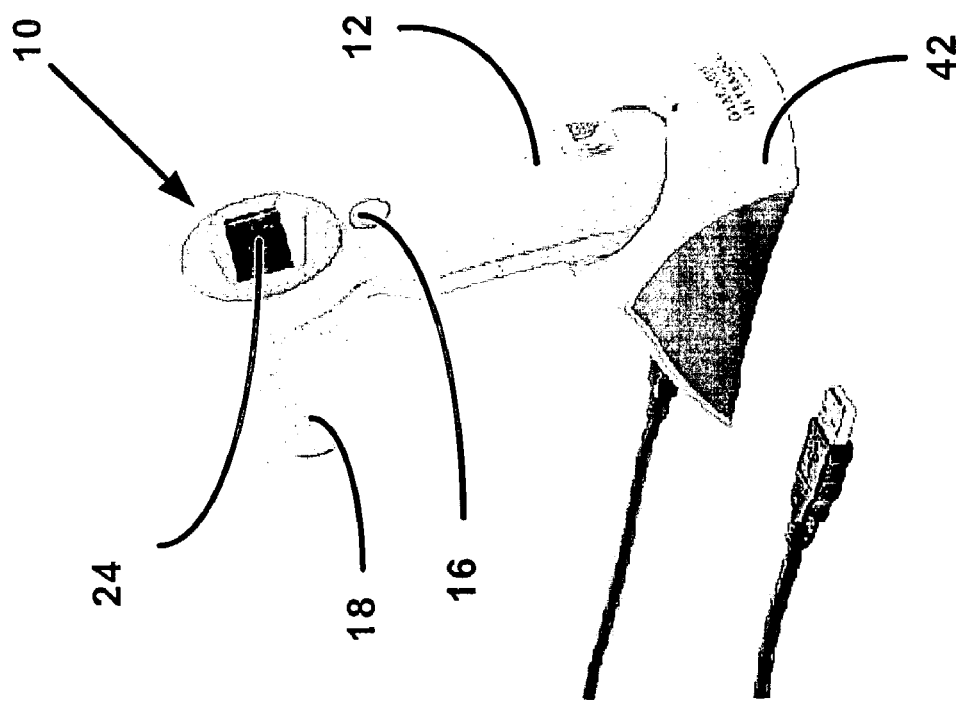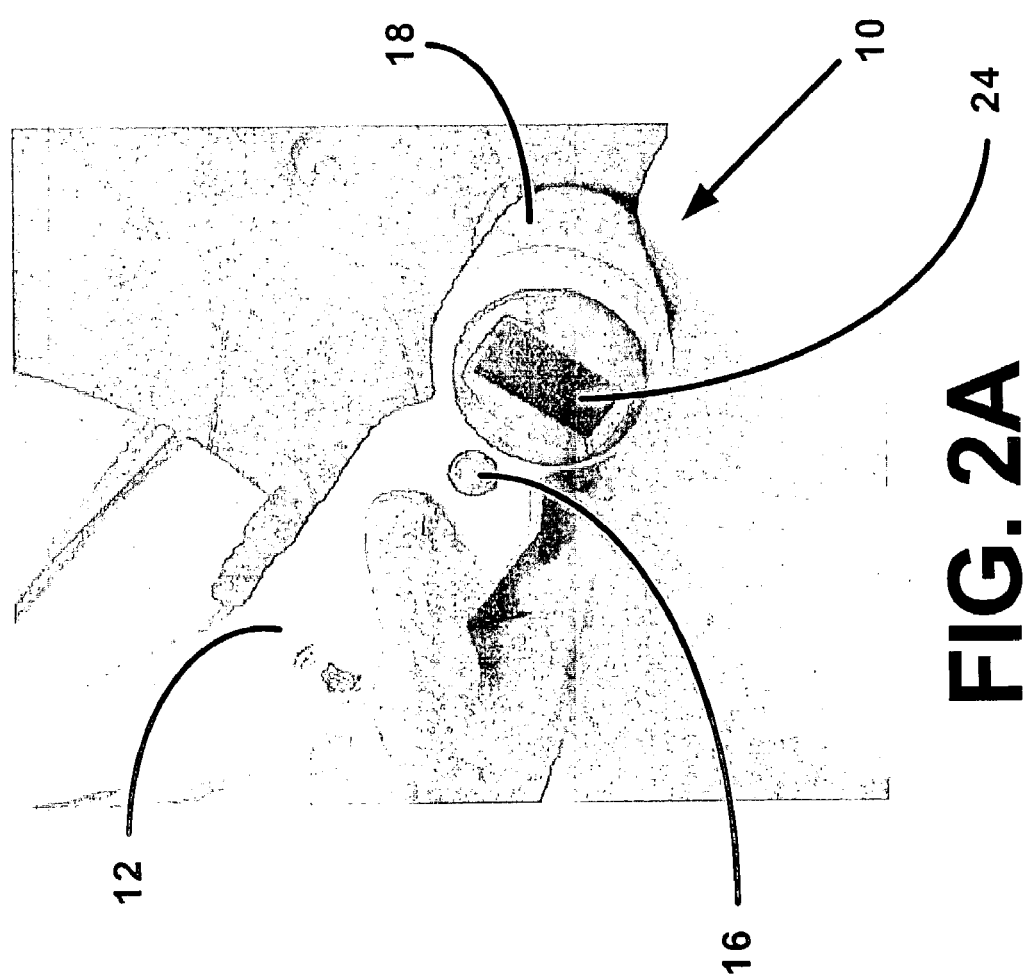

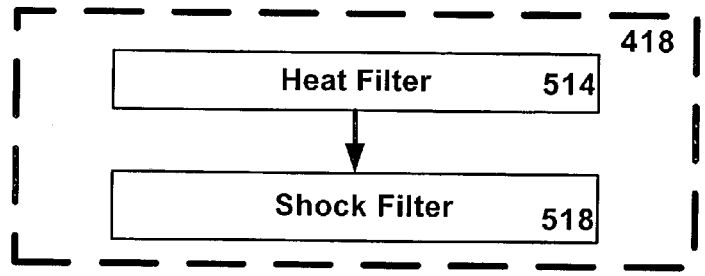
FIG. 8A
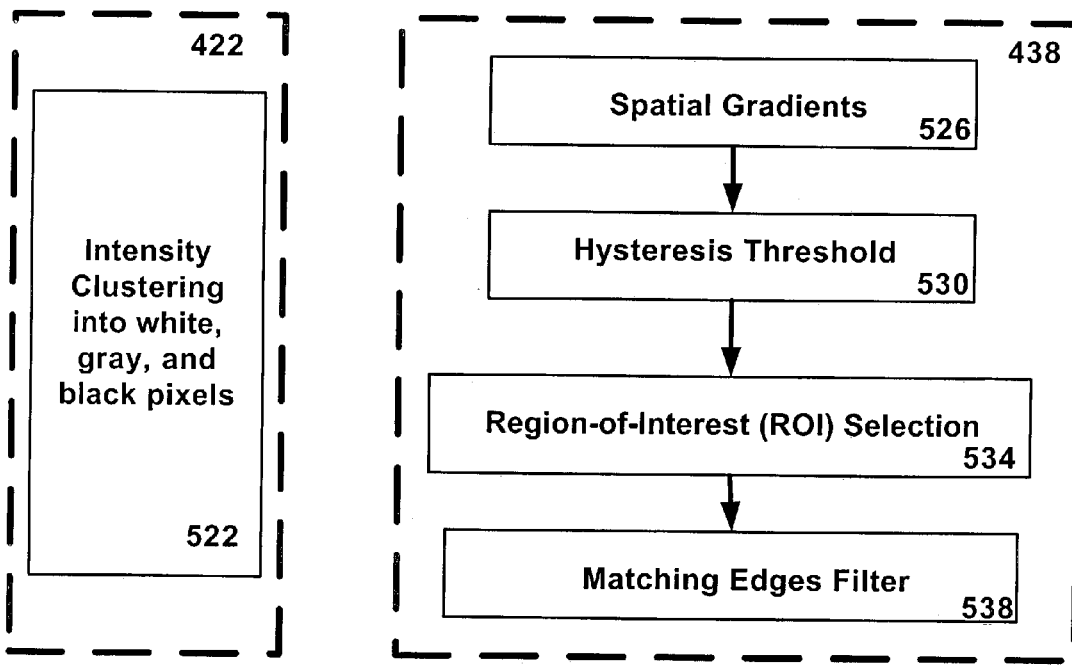
FIG. 8B  FIG. 8C

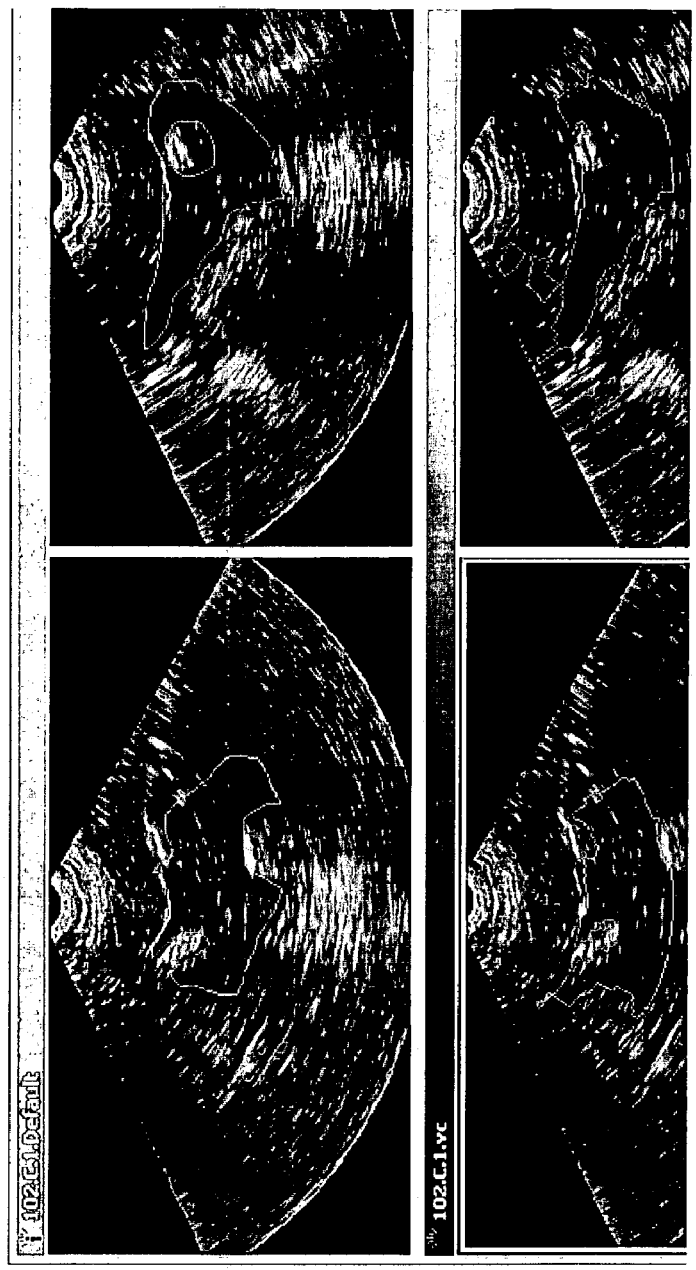

3D ULTRASOUND-BASED INSTRUMENT FOR NON-INVASIVE MEASUREMENT OF AMNIOTIC FLUID VOLUME

PRIORITY CLAIM

This invention claims priority to provisional patent application Ser. No. 60/423,881 filed Nov. 5, 2002, and to provisional patent application Ser. No. 60/400,624, filed Aug. 2, 2002.

FIELD OF THE INVENTION

This invention pertains to the field of obstetrics, particularly to ultrasound-based non-invasive obstetric measurements.

BACKGROUND OF THE INVENTION

Measurement of the amount of Amniotic Fluid (AF) volume is critical for assessing the kidney and lung function of a fetus and also for assessing the placental function of the mother. Amniotic fluid volume is also a key measure to diagnose conditions such as polyhydramnios (too much AF) and oligohydramnios (too little AF). Polyhydramnios and oligohydramnios are diagnosed in about 7–8% of all pregnancies and these conditions are of concern because they may lead to birth defects or to delivery complications. The amniotic fluid volume is also one of the important components of the fetal biophysical profile, a major indicator of fetal well-being.

The currently practiced and accepted method of quantitatively estimating the AF volume is from two-dimensional (2D) ultrasound images. The most commonly used measure is known as the use of the amniotic fluid index (AFI). AFI is the sum of vertical lengths of the largest AF pockets in each of the 4 quadrants. The four quadrants are defined by the umbilicus (the navel) and the linea nigra (the vertical mid-line of the abdomen). The transducer head is placed on the maternal abdomen along the longitudinal axis with the patient in the supine position. This measure was first proposed by Phelan et al (Phelan J P, Smith C V, Broussard P, Small M., "Amniotic fluid volume assessment with the four-quadrant technique at 36–42 weeks' gestation," J Reprod Med July; 32(7): 540–2, 1987) and then recorded for a large normal population over time by Moore and Cayle (Moore T R, Cayle J E. "The amniotic fluid index in normal human pregnancy," Am J Obstet Gynecol May; 162(5): 1168–73, 1990).

Even though the AFI measure is routinely used, studies have shown a very poor correlation of the AFI with the true AF volume (Sepulveda W, Flack N J, Fisk N M., "Direct volume measurement at midtrimester amnioinfusion in relation to ultrasonographic indexes of amniotic fluid volume," Am J Obstet Gynecol April; 170(4): 1160–3, 1994). The correlation coefficient was found to be as low as 0.55, even for experienced sonographers. The use of vertical diameter only and the use of only one pocket in each quadrant are two reasons why the AFI is not a very good measure of AF Volume (AFV).

Some of the other methods that have been used to estimate AF volume include:

Dye dilution technique. This is an invasive method where a dye is injected into the AF during amniocentesis and the final concentration of dye is measured from a sample of AF removed after several minutes. This technique is the accepted gold standard for AF volume measurement; however, it is an invasive and cumbersome method and is not routinely used.

Subjective interpretation from ultrasound images. This technique is obviously dependent on observer experience and has not been found to be very good or consistent at diagnosing oligo- or poly-hydramnios.

Vertical length of the largest single cord-free pocket. This is an earlier variation of the AFI where the diameter of only one pocket is measured to estimate the AF volume.

Two-diameter areas of the largest AF pockets in the four quadrants. This is similar to the AFI; however, in this case, two diameters are measured instead of only one for the largest pocket. This two diameter area has been recently shown to be better than AFI or the single pocket measurement in identifying oligohydramnios (Magann E F, Perry K G Jr, Chauhan S P, Anfanger P J, Whitworth N S, Morrison J C., "The accuracy of ultrasound evaluation of amniotic fluid volume in singleton pregnancies: the effect of operator experience and ultrasound interpretative technique," J Clin Ultrasound, June; 25(5):249–53, 1997).

The measurement of various anatomical structures using computational constructs are described, for example, in U.S. Pat. No. 6,346,124 to Geiser, et al. (Autonomous Boundary Detection System For Echocardiographic Images). Similarly, the measurement of bladder structures are covered in U.S. Pat. No. 6,213,949 to Ganguly, et al. (System For Estimating Bladder Volume) and U.S. Pat. No. 5,235,985 to McMorrow, et al., (Automatic Bladder Scanning Apparatus). The measurement of fetal head structures is described in U.S. Pat. No. 5,605,155 to Chalana, et al., (Ultrasound System For Automatically Measuring Fetal Head Size). The measurement of fetal weight is described in U.S. Pat. No. 6,375,616 to Soferman, et al. (Automatic Fetal Weight Determination).

Pertaining to ultrasound-based determination of amniotic fluid volumes, Segiv et al. (in Segiv C, Akselrod S, Tepper R., "Application of a semiautomatic boundary detection algorithm for the assessment of amniotic fluid quantity from ultrasound images." Ultrasound Med Biol, May, 25(4): 515–26, 1999) describe a method for amniotic fluid segmentation from 2D images. However, the Segiv et al. method is interactive in nature and the identification of amniotic fluid volume is very observer dependent. Moreover, the system described is not a dedicated device for amniotic fluid volume assessment.

Grover et al. (Grover J, Mentakis E A, Ross M G, "Three-dimensional method for determination of amniotic fluid volume in intrauterine pockets." Obstet Gynecol, December; 90(6): 1007–10, 1997) describe the use of a urinary bladder volume instrument for amniotic fluid volume measurement. The Grover et al. method makes use of the bladder volume instrument without any modifications and uses shape and other anatomical assumptions specific to the bladder that do not generalize to amniotic fluid pockets. Amniotic fluid pockets having shapes not consistent with the Grover et al. bladder model introduces analytical errors. Moreover, the bladder volume instrument does not allow for the possibility of more than one amniotic fluid pocket in one image scan. Therefore, the amniotic fluid volume measurements made by the Grover et al. system may not be correct or accurate.

None of the currently used methods for AF volume estimation are ideal. Therefore, there is a need for better, non-invasive, and easier ways to accurately measure amniotic fluid volume.

SUMMARY OF THE INVENTION

The preferred form of the invention is a three dimensional (3D) ultrasound-based system and method having a plurality of automated processes optimized to robustly locate and measure the volume of amniotic fluid in a uterus without resorting to pre-conceived models of the shapes of amniotic fluid pockets in ultrasound images. The automated process uses a plurality of algorithms in a sequence that includes steps for image enhancement, segmentation, and polishing.

A hand-held 3D ultrasound device is used to image the uterus trans-abdominally. The user moves the device around on the maternal abdomen and, using 2D image processing to locate the amniotic fluid areas, the device gives feedback to the user about where to acquire the 3D image data sets. The user acquires one or more 3D image data sets covering all of the amniotic fluid in the uterus and the data sets are then stored in the device or transferred to a host computer.

The 3D datasets are then subjected to a 3D analysis process, the 3D analysis process preferably having a plurality of processes to calculate and the total volume of amniotic fluid in the uterus. The plurality of processes is either implemented on the device itself or is implemented on the host computer. Alternatively, the plurality of processes can also be implemented on a server or other computer to which the 3D ultrasound data sets are transferred.

In one preferred 3D analysis process, each 2D image in the 3D dataset is first enhanced using non-linear filters by an image pre-filtering step. The image pre-filtering step includes an image-smoothing step to reduce image noise followed by an image-sharpening step to obtain maximum contrast between organ wall boundaries.

A second process includes subjecting the resulting image of the first process to a location method to identify initial edge points between amniotic fluid and other fetal or maternal structures. The location method automatically determines the leading and trailing regions of wall locations along an A-mode one-dimensional scan line.

A third process includes subjecting the image of the first process to an intensity-based segmentation process where dark pixels (representing fluid) are automatically separated from bright pixels (representing tissue and other structures).

In a fourth process, the images resulting from the second and third step are combined to result in a single image representing likely amniotic fluid regions.

In a fifth process, the combined image is cleaned to make the output image smooth and to remove extraneous structures such as the fetal head and the fetal bladder.

Finally, a sixth process includes placing boundary line contours on each 2D image. Thereafter, the method then calculates the total 3D volume of amniotic fluid.

The system and method further provides an automatic method to detect and correct for any contribution the fetal head provides to the amniotic fluid volume.

BRIEF DESCRIPTION OF THE DRAWINGS

FIG. 2A is a is depiction of the hand-held transceiver in use for scanning a patient;

FIG. 2B is a perspective view of the hand-held transceiver device sitting in a communication cradle;

FIG. 8A depicts the sub-algorithms of Image Enhancement;

FIG. 8B depicts the sub-algorithms of Intensity-Based Segmentation;

FIG. 8C depicts the sub-algorithms of Edge-Based Segmentation;

FIG. 12 presents a 4-panel series of sonographer amniotic fluid pocket outlines and the algorithm output amniotic fluid pocket outlines.

DETAILED DESCRIPTION OF THE PREFERRED EMBODIMENT

Figure 1:
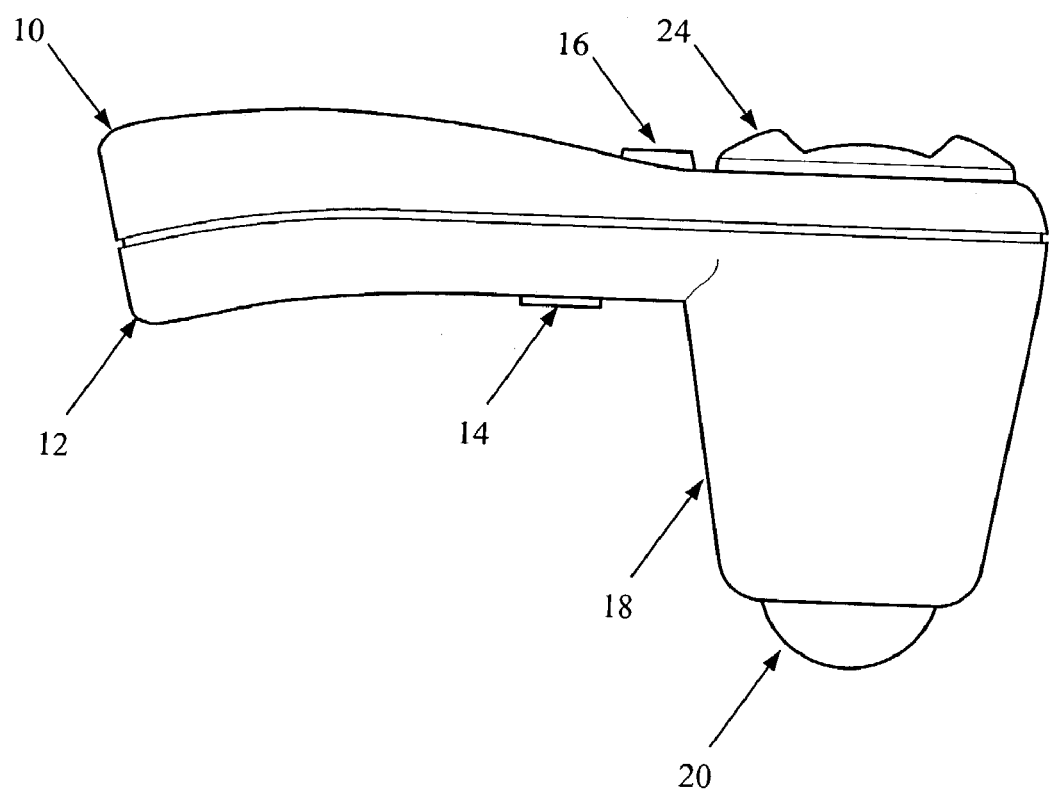
FIG. 1 is a side view of a microprocessor-controlled, hand-held ultrasound transceiver.

The preferred portable embodiment of the ultrasound transceiver of the amniotic fluid volume measuring system are shown in FIGS. 1–4. The transceiver 10 includes a handle 12 having a trigger 14 and a top button 16, a transceiver housing 18 attached to the handle 12, and a transceiver dome 20. A display 24 for user interaction is attached to the transceiver housing 18 at an end opposite the transceiver dome 20. Housed within the transceiver 10 is a single element transducer (not shown) that converts ultrasound waves to electrical signals. The transceiver 10 is held in position against the body of a patient by a user for image acquisition and signal processing. In operation, the transceiver 10 transmits a radio frequency ultrasound signal at substantially 3.7 MHz to the body and then receives a returning echo signal. To accommodate different patients having a variable range of obesity, the transceiver 10 can be adjusted to transmit a range of probing ultrasound energy from approximately 2 MHz to approximately 10 MHz radio frequencies.

The top button 16 selects for different acquisition volumes. The transceiver is controlled by a microprocessor and software associated with the microprocessor and a digital signal processor of a computer system. As used in this invention, the term "computer system" broadly comprises any microprocessor-based or other computer system capable of executing operating instructions and manipulating data, and is not limited to a traditional desktop or notebook computer. The display 24 presents alphanumeric or graphic data indicating the proper or optimal positioning of the transceiver 10 for initiating a series of scans. A suitable transceiver is the DCD372 made by Diagnostic Ultrasound. In alternate embodiments, the two- or three-dimensional image of a scan plane may be presented in the display 24.

Although the preferred ultrasound transceiver is described above, other transceivers may also be used. For example, the transceiver need not be battery-operated or otherwise portable, need not have a top-mounted display 24, and may include many other features or differences. The display 24 may be a liquid crystal display (LCD), a light emitting diode (LED), a cathode ray tube (CRT), or any suitable display capable of presenting alphanumeric data or graphic images.

FIG. 2A is a photograph of the hand-held transceiver 10 for scanning a patient. The transceiver 10 is then positioned over the patient's abdomen by a user holding the handle 12 to place the transceiver housing 18 against the patient's abdomen. The top button 16 is centrally located on the handle 12. Once optimally positioned over the abdomen for scanning, the transceiver 10 transmits an ultrasound signal at substantially 3.7 MHz into the uterus. The transceiver 10 receives a return ultrasound echo signal emanating from the uterus and presents it on the display 24.

FIG. 2B is a perspective view of the hand-held transceiver device sitting in a communication cradle. The transceiver 10 sits in a communication cradle 42 via the handle 12. This cradle can be connected to a standard USB port of any personal computer, enabling all the data on the device to be transferred to the computer and enabling new programs to be transferred into the device from the computer.

Figure 3:
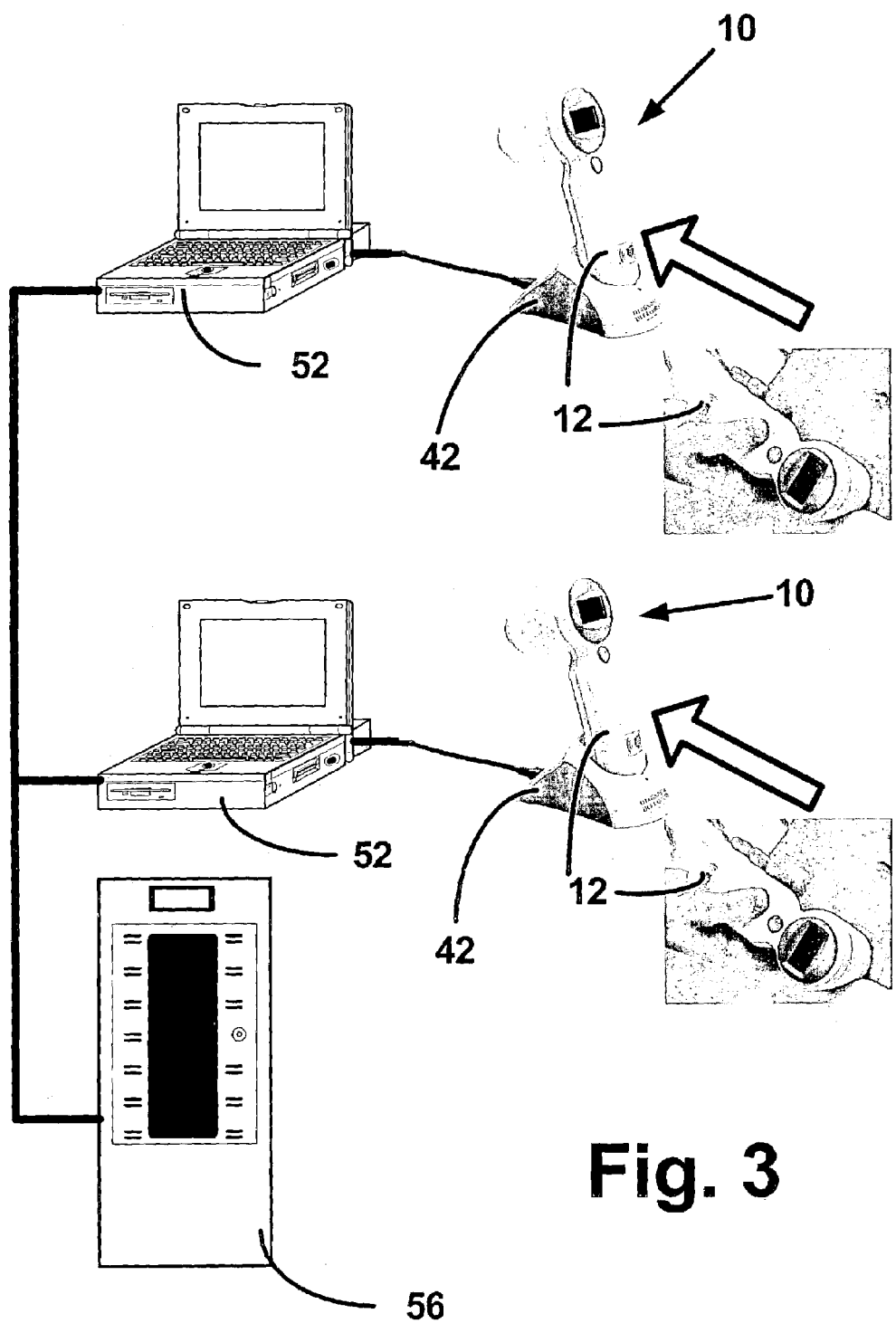
FIG. 3 depicts a schematic view of a plurality of transceivers in connection with a server.

FIG. 3 depicts a schematic view of a plurality of transceivers in connection with a server. FIG. 3, by example, depicts each transceiver 10 being used to send probing ultrasound radiation to a uterus of a patient and to subsequently retrieve ultrasound echoes returning from the uterus, convert the ultrasound echoes into digital echo signals, store the digital echo signals, and process the digital echo signals by algorithms of the invention. A user holds the transceiver 10 by the handle 12 to send probing ultrasound signals and to receive incoming ultrasound echoes. The transceiver 10 is placed in the communication cradle 42 that is in signal communication with a computer 52, and operates as an amniotic fluid volume measuring system. Two amniotic fluid volume-measuring systems are depicted as representative though fewer or more systems may be used. As used in this invention, a "server" can be any computer software or hardware that responds to requests or issues commands to or from a client. Likewise, the server may be accessible by one or more client computers via the Internet, or may be in communication over a LAN or other network.

Each amniotic fluid volume measuring systems includes the transceiver 10 for acquiring data from a patient. The transceiver 10 is placed in the cradle 52 to establish signal communication with the computer 52. Signal communication as illustrated is by a wired connection from the cradle 42 to the computer 52. Signal communication between the transceiver 10 and the computer 52 may also be by wireless means, for example, infrared signals or radio frequency signals. The wireless means of signal communication may occur between the cradle 42 and the computer 52, the transceiver 10 and the computer 52, or the transceiver 10 and the cradle 42.

A preferred first embodiment of the amniotic fluid volume measuring system includes each transceiver 10 being separately used on a patient and sending signals proportionate to the received and acquired ultrasound echoes to the computer 52 for storage. Residing in each computer 52 are imaging programs having instructions to prepare and analyze a plurality of one dimensional (1D) images from the stored signals and transforms the plurality of 1D images into the plurality of 2D scanplanes. The imaging programs also present 3D renderings from the plurality of 2D scanplanes. Also residing in each computer 52 are instructions to perform the additional ultrasound image enhancement procedures, including instructions to implement the image processing algorithms.

A preferred second embodiment of the amniotic fluid volume measuring system is similar to the first embodiment, but the imaging programs and the instructions to perform the additional ultrasound enhancement procedures are located on the server 56. Each computer 52 from each amniotic fluid volume measuring system receives the acquired signals from the transceiver 10 via the cradle 51 and stores the signals in the memory of the computer 52. The computer 52 subsequently retrieves the imaging programs and the instructions to perform the additional ultrasound enhancement procedures from the server 56. Thereafter, each computer 52 prepares the 1D images, 2D images, 3D renderings, and enhanced images from the retrieved imaging and ultrasound enhancement procedures. Results from the data analysis procedures are sent to the server 56 for storage.

A preferred third embodiment of the amniotic fluid volume measuring system is similar to the first and second embodiments, but the imaging programs and the instructions to perform the additional ultrasound enhancement procedures are located on the server 56 and executed on the server 56. Each computer 52 from each amniotic fluid volume measuring system receives the acquired signals from the transceiver 10 and via the cradle 51 sends the acquired signals in the memory of the computer 52. The computer 52 subsequently sends the stored signals to the server 56. In the server 56, the imaging programs and the instructions to perform the additional ultrasound enhancement procedures are executed to prepare the 1D images, 2D images, 3D renderings, and enhanced images from the server 56 stored signals. Results from the data analysis procedures are kept on the server 56, or alternatively, sent to the computer 52.

Figure 4:
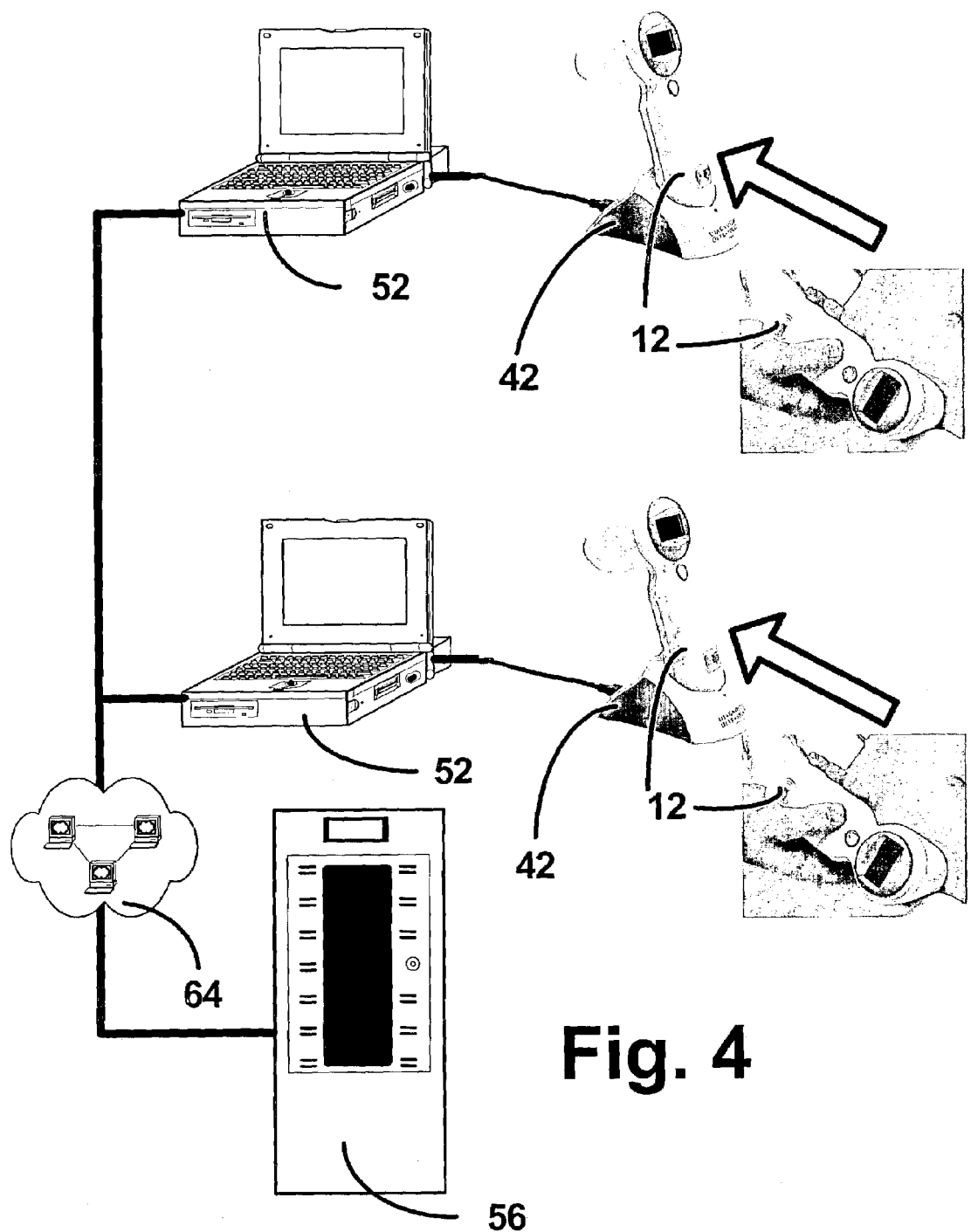
FIG. 4 depicts a schematic view of a plurality of transceivers in connection with a server over a network.

FIG. 4 is a schematic view of a plurality of amniotic fluid measuring systems connected to a server over the Internet or other network 64. FIG. 4 represents any of the first, second, or third embodiments of the invention advantageously deployed to other servers and computer systems through connections via the network.

Figures 5A, 5B:
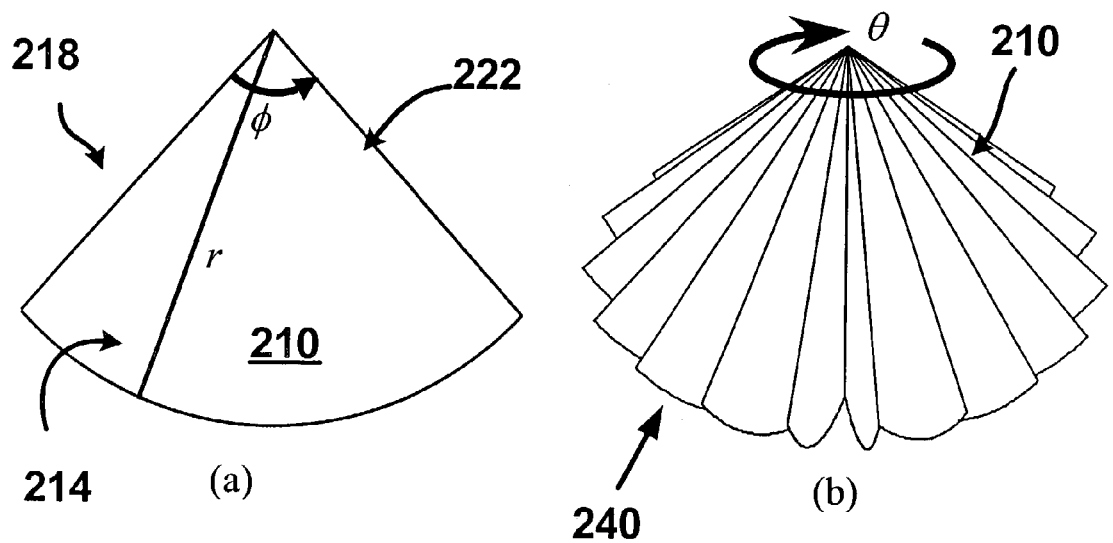
FIG. 5A a graphical representation of a plurality of scan lines forming a single scan plane.
FIG. 5B is a graphical representation of a plurality of scanplanes forming a three-dimensional array having a substantially conic shape.

FIG. 5A a graphical representation of a plurality of scan lines forming a single scan plane. FIG. 5A illustrates how ultrasound signals are used to make analyzable images, more specifically how-a series of one-dimensional (1D) scanlines are used to produce a two-dimensional (2D) image. The 1D and 2D operational aspects of the single element tranducer housed in the transceiver 10 is seen as it rotates mechanically about an angle $\phi$. A scanline 214 of length r migrates between a first limiting position 218 and a second limiting position 222 as determined by the value of the angle $\phi$, creating a fan-like 2D scanplane 210. In one preferred form, the transceiver 10 operates substantially at 3.7 MHz frequency and creates an approximately 18 cm deep scan line 214 and migrates within the angle $\phi$ having an angle of approximately 0.027 radians. A first motor tilts the transducer approximately 60° clockwise and then counterclockwise forming the fan-like 2D scanplane presenting an approximate 120° 2D sector image. A plurality of scanlines, each scanline substantially equivalent to scanline 214 is recorded, between the first limiting position 218 and the second limiting position 222 formed by the unique tilt angle φ. The plurality of scanlines between the two extremes forms a scanplane 210. In the preferred embodiment, each scanplane contains 77 scan lines, although the number of lines can vary within the scope of this invention. The tilt angle φ sweeps through angles approximately between −60° and +60° for a total arc of approximately 120°.

FIG. 5B is a graphical representation of a plurality of scanplanes forming a three-dimensional array (3D) 240 having a substantially conic shape. FIG. 5B illustrates how a 3D rendering is obtained from the plurality of 2D scanplanes. Within each scanplane 210 are the plurality of scanlines, each scanline equivalent to the scanline 214 and sharing a common rotational angle θ. In the preferred embodiment, each scanplane contains 77 scan lines, although the number of lines can vary within the scope of this invention. Each 2D sector image scanplane 210 with tilt angle φ and range r (equivalent to the scanline 214) collectively forms a 3D conic array 240 with rotation angle θ. After gathering the 2D sector image, a second motor rotates the transducer between 3.75° or 7.5° to gather the next 120° sector image. This process is repeated until the transducer is rotated through 180°, resulting in the cone-shaped 3D conic array 240 data set with 24 planes rotationally assembled in the preferred embodiment. The conic array could have fewer or more planes rotationally assembled. For example, preferred alternate embodiments of the conic array could include at least two scanplanes, or a range of scanplanes from 2 to 48 scanplanes. The upper range of the scanplanes can be greater than 48 scanplanes. The tilt angle φ indicates the tilt of the scanline from the centerline in 2D sector image, and the rotation angle θ, identifies the particular rotation plane the sector image lies in. Therefore, any point in this 3D data set can be isolated using coordinates expressed as three parameters, P(r, φ, θ).

As the scanlines are transmitted and received, the returning echoes are interpreted as analog electrical signals by a transducer, converted to digital signals by an analog-to-digital converter, and conveyed to the digital signal processor of the computer system for storage and analysis to determine the locations of the amniotic fluid walls. The computer system is representationally depicted in FIGS. 3 and 4 and includes a microprocessor, random access memory (RAM), or other memory for storing processing instructions and data generated by the transceiver 10.

Figure 6:
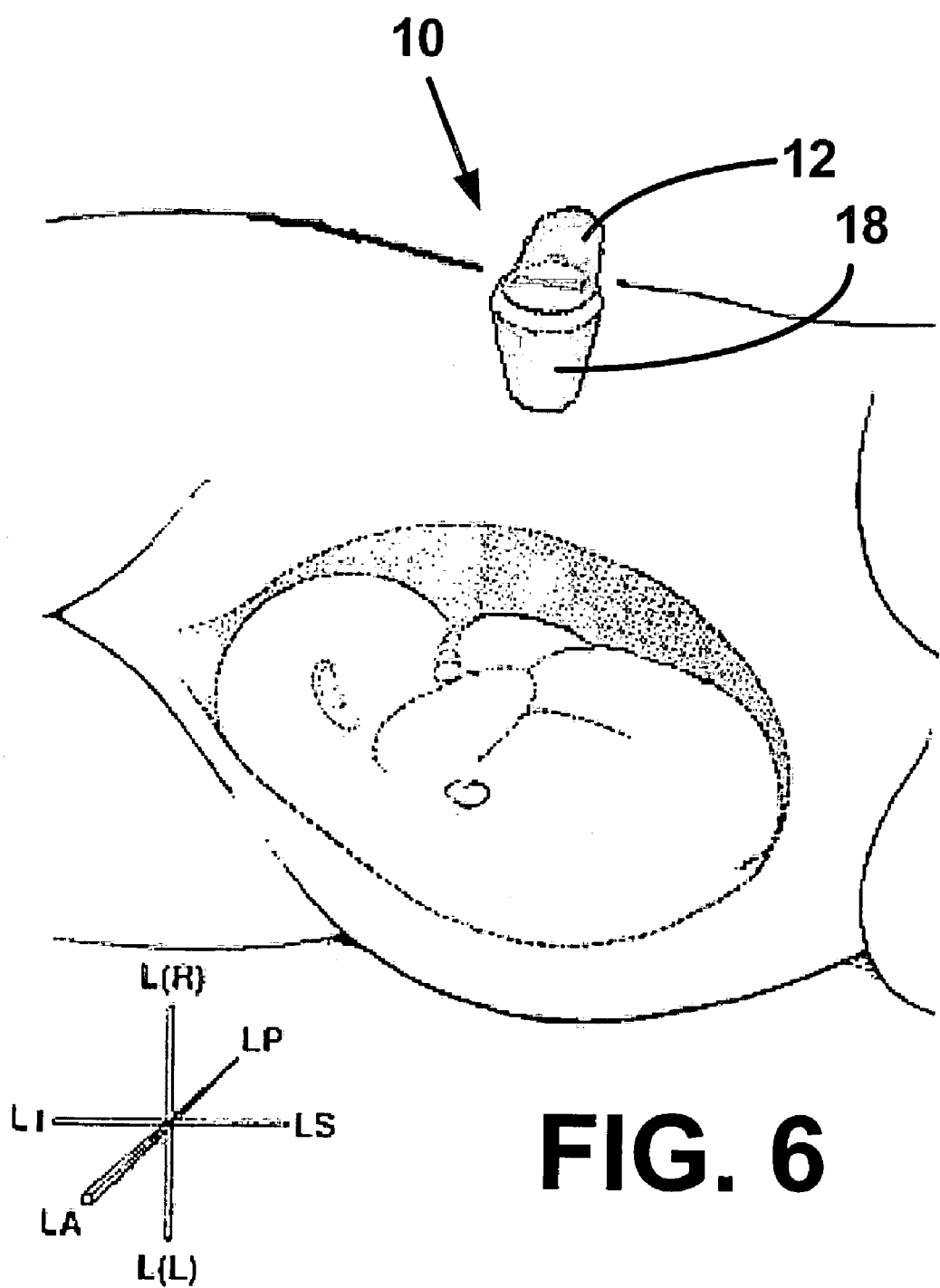
FIG. 6 is a depiction of the hand-held transceiver placed laterally on a patient trans-abdominally to transmit ultrasound and receive ultrasound echoes for processing to determine amniotic fluid volumes.

FIG. 6 is a depiction of the hand-held transceiver placed on a patient trans-abdominally to transmit probing ultrasound and receive ultrasound echoes for processing to determine amniotic fluid volumes. The transceiver 10 is held by the handle 12 to position over a patient to measure the volume of amniotic fluid in an amniotic sac over a baby. A plurality of axes for describing the orientation of the baby, the amniotic sac, and mother is illustrated. The plurality of axes includes a vertical axis depicted on the line L(R)-L(L) for left and right orientations, a horizontal axis LI-LS for inferior and superior orientations, and a depth axis LA-LP for anterior and posterior orientations.

FIG. 6 is representative of a preferred data acquisition protocol used for amniotic fluid volume determination. In this protocol, the transceiver 10 is the hand-held 3D ultrasound device (for example, model DCD372 from Diagnostic Ultrasound) and is used to, image the uterus trans-abdominally. Initially during the targeting phase, the patient is in a supine position and the device is operated in a 2D continuous acquisition mode. A 2D continuous mode is where the data is continuously acquired in 2D and presented as a scanplane similar to the scanplane 210 on the display 24 while an operator physically moves the transceiver 10. An operator moves the transceiver 10 around on the maternal abdomen and the presses the trigger 14 of the transceiver 10 and continuously acquires real-time feedback presented in 2D on the display 24. Amniotic fluid, where present, visually appears as dark regions along with an alphanumeric indication of amniotic fluid area (for example, in $cm^2$) on the display 24. Based on this real-time information in terms of the relative position of the transceiver 10 to the fetus, the operator decides which side of the uterus has more amniotic fluid by the presentation on the display 24. The side having more amniotic fluid presents as regions having larger darker regions on the display 24. Accordingly, the side displaying a large dark region registers greater alphanumeric area while the side with less fluid shows displays smaller dark regions and proportionately registers smaller alphanumeric area on the display 24. While amniotic fluid is present throughout the uterus, its distribution in the uterus depends upon where and how the fetus is positioned within the uterus. There is usually less amniotic fluid around the fetus's spine and back and more amniotic fluid in front of its abdomen and around the limbs.

Based on fetal position information acquired from data gathered under continuous acquisition mode, the patient is placed in a lateral recumbent position such that the fetus is displaced towards the ground creating a large pocket of amniotic fluid close to abdominal surface where the transceiver 10 can be placed as shown in FIG. 6. For example, if large fluid pockets are found on the right side of the patient, the patient is asked to turn with the left side down and if large fluid pockets are found on the left side, the patient is asked to turn with the right side down.

After the patient has been placed in the desired position, the transceiver 10 is again operated in the 2D continuous acquisition mode and is moved around on the lateral surface of the patient's abdomen. The operator finds the location that shows the largest amniotic fluid area based on acquiring the largest dark region imaged and the largest alphanumeric value displayed on the display 24. At the lateral abdominal location providing the largest dark region, the transceiver 10 is held in a fixed position, the trigger 14 is released to acquire a 3D image comprising a set of arrayed scanplanes. The 3D image presents a rotational array of the scanplanes 210 similar to the 3D array 240. In a preferred alternate data acquisition protocol, the operator can reposition the transceiver 10 to a different abdominal location to acquire new 3D images comprised of different scanplane arrays similar to the 3D array 240. Multiple scan cones obtained from different lateral positions provide the operator the ability to verify amniotic fluid imaging and measurement. In the case of a single image cone being too small to accommodate a large AFV measurement, obtaining multiple 3D array 240 image cones ensures that the total volume of large AFV regions is determined. Multiple 3D images may also be acquired by pressing the top bottom 16 to select multiple conic arrays similar to the 3D array 240.

Depending on the position of the fetus relative to the location of the transceiver 10, a single image scan may present an underestimated volume of AFV due to amniotic fluid pockets that remain hidden behind the limbs of the fetus. The hidden amniotic fluid pockets present as unquantifiable shadow-regions.

To guard against underestimating AFV, repeated positioning the transceiver 10 and rescanning can be done to obtain more than one ultrasound view to maximize detection of amniotic fluid pockets. Repositioning and rescanning provides multiple views as a plurality of the 3D arrays 240 images cones. Acquiring multiple images cones improves the probability of obtaining initial estimates of AFV that otherwise could remain undetected and un-quantified in a single scan.

In an alternative scan protocol, the user determines and scans at only one location on the entire abdomen that shows the maximum amniotic fluid area while the patient is the supine position. As before, when the user presses the top button 16, 2D scanplane images equivalent to the scanplane 210 are continuously acquired and the amniotic fluid area on every image is automatically computed. The user selects one location that shows the maximum amniotic fluid area. At this location, as the user releases the scan button, a full 3D data cone is acquired and stored in the device's memory.

Figure 7:
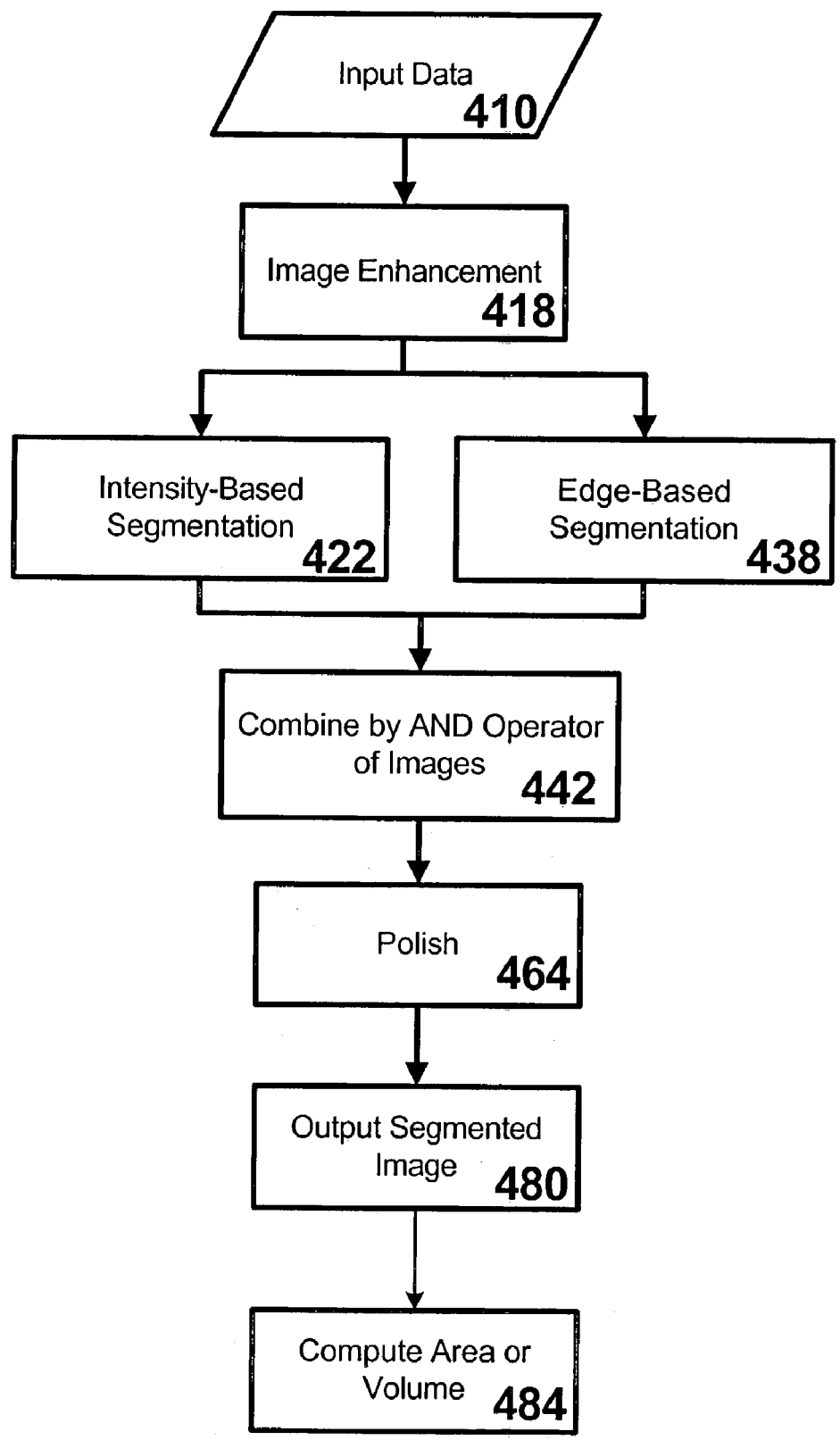
FIG. 7 shows a block diagram overview of the two-dimensional and three-dimensional Input, Image Enhancement, Intensity-Based Segmentation, Edge-Based Segmentation, Combine, Polish, Output, and Compute algorithms to visualize and determine the volume or area of amniotic fluid.

FIG. 7 shows a block diagram overview the image enhancement, segmentation, and polishing algorithms of the amniotic fluid volume measuring system. The enhancement, segmentation, and polishing algorithms are applied to each scanplane 210 or to the entire scan cone 240 to automatically obtain amniotic fluid regions. For scanplanes substantially equivalent to scanplane 210, the algorithms are expressed in two-dimensional terms and use formulas to convert scanplane pixels (picture elements) into area units. For the scan cones substantially equivalent to the 3D conic array 240, the algorithms are expressed in three-dimensional terms and use formulas to convert voxels (volume elements) into volume units.

The algorithms expressed in 2D terms are used during the targeting phase where the operator trans-abdominally positions and repositions the transceiver 10 to obtain real-time feedback about the amniotic fluid area in each scanplane. The algorithms expressed in 3D terms are used to obtain the total amniotic fluid volume computed from the voxels contained within the calculated amniotic fluid regions in the 3D conic array 240.

FIG. 7 represents an overview of a preferred method of the invention and includes a sequence of algorithms, many of which have sub-algorithms described in more specific detail in FIGS. 8A–F. FIG. 7 begins with inputting data of an unprocessed image at step 410. After unprocessed image data 410 is entered (e.g., read from memory, scanned, or otherwise acquired), it is automatically subjected to an image enhancement algorithm 418 that reduces the noise in the data (including speckle noise) using one or more equations while preserving the salient edges on the image using one or more additional equations. Next, the enhanced images are segmented by two different methods whose results are eventually combined. A first segmentation method applies an intensity-based segmentation algorithm 422 that determines all pixels that are potentially fluid pixels based on their intensities. A second segmentation method applies an edge-based segmentation algorithm 438 that relies on detecting the fluid and tissue interfaces. The images obtained by the first segmentation algorithm 422 and the images obtained by the second segmentation algorithm 438 are brought together via a combination algorithm 442 to provide a substantially segmented image. The segmented image obtained from the combination algorithm 442 are then subjected to a polishing algorithm 464 in which the segmented image is cleaned-up by filling gaps with pixels and removing unlikely regions. The image obtained from the polishing algorithm 464 is outputted 480 for calculation of areas and volumes of segmented regions-of-interest. Finally the area or the volume of the segmented region-of-interest is computed 484 by multiplying pixels by a first resolution factor to obtain area, or voxels by a second resolution factor to obtain volume. For example, for pixels having a size of 0.8 mm by 0.8 mm, the first resolution or conversion factor for pixel area is equivalent to 0.64 $mm^2$, and the second resolution or conversion factor for voxel volume is equivalent to 0.512 $mm^3$. Different unit lengths for pixels and voxels may be assigned, with a proportional change in pixel area and voxel volume conversion factors.

The enhancement, segmentation and polishing algorithms depicted in FIG. 7 for measuring amniotic fluid areas or volumes are not limited to scanplanes assembled into rotational arrays equivalent to the 3D array 240. As additional examples, the enhancement, segmentation and polishing algorithms depicted in FIG. 7 apply to translation arrays and wedge arrays. Translation arrays are substantially rectilinear image plane slices from incrementally repositioned ultrasound transceivers that are configured to acquire ultrasound rectilinear scanplanes separated by regular or irregular rectilinear spaces. The translation arrays can be made from transceivers configured to advance incrementally, or may be hand-positioned incrementally by an operator. The operator obtains a wedge array from ultrasound transceivers configured to acquire wedge-shaped scanplanes separated by regular or irregular angular spaces, and either mechanistically advanced or hand-tilted incrementally. Any number of scanplanes can be either translationally assembled or wedge-assembled ranges, but preferably in ranges greater than 2 scanplanes.

Other preferred embodiments of the enhancement, segmentation and polishing algorithms depicted in FIG. 7 may be applied to images formed by line arrays, either spiral distributed or reconstructed random-lines. The line arrays are defined using points identified by the coordinates expressed by the three parameters, $P(r,\phi,\theta)$, where the values or $r$, $\phi$, and $\theta$ can vary.

The enhancement, segmentation and polishing algorithms depicted in FIG. 7 are not limited to ultrasound applications but may be employed in other imaging technologies utilizing scanplane arrays or individual scanplanes. For example, biological-based and non-biological-based images acquired using infrared, visible light, ultraviolet light, microwave, x-ray computed tomography, magnetic resonance, gamma rays, and positron emission are images suitable for the algorithms depicted in FIG. 7. Furthermore, the algorithms depicted in FIG. 7 can be applied to facsimile transmitted images and documents.

FIGS. 8A–E depict expanded details of the preferred embodiments of enhancement, segmentation, and polishing algorithms described in FIG. 7. Each of the following greater detailed algorithms are either implemented on the transceiver 10 itself or are implemented on the host computer 52 or on the server 56 computer to which the ultrasound data is transferred.

FIG. 8A depicts the sub-algorithms of Image Enhancement. The sub-algorithms include a heat filter 514 to reduce noise and a shock filter 518 to sharpen edges. A combination of the heat and shock filters works very well at reducing noise and sharpening the data while preserving the significant discontinuities. First, the noisy signal is filtered using a 1D heat filter (Equation E1 below), which results in the reduction of noise and smoothing of edges. This step is followed by a shock-filtering step 518 (Equation E2 below), which results in the sharpening of the blurred signal. Noise reduction and edge sharpening is achieved by application of the following equations E1–E2. The algorithm of the heat filter 514 uses a heat equation E1. The heat equation E1 in partial differential equation (PDE) form for image processing is expressed as:

$$\frac{\partial u}{\partial t} = \frac{\partial^2 u}{\partial x^2} + \frac{\partial^2 u}{\partial y^2}, \quad \text{E1}$$

where u is the image being processed. The image u is 2D, and is comprised of an array of pixels arranged in rows along the x-axis, and an array of pixels arranged in columns along the y-axis, The pixel intensity of each pixel in the image u has an initial input image pixel intensity (I) defined as $u_0$=I. The value of I depends on the application, and commonly occurs within ranges consistent with the application. For example, I can be as low as 0 to 1, or occupy middle ranges between 0 to 127 or 0 to 512. Similarly, I may have values occupying higher ranges of 0 to 1024 and 0 to 4096, or greater.

The heat equation E1 results in a smoothing of the image and is equivalent to the Gaussian filtering of the image. The larger the number of iterations that it is applied for the more the input image is smoothed or blurred and the more the noise that is reduced.

The shock filter 518 is a PDE used to sharpen images as detailed below. The two dimensional shock filter E2 is expressed as:

$$\frac{\partial u}{\partial t} = -F(l(u))\|\nabla u\|, \quad \text{E2}$$

where u is the image processed whose initial value is the input image pixel intensity (I): $u_0$=I where the l(u) term is the Laplacian of the image u, F is a function of the Laplacian, and $\|\nabla u\|$ is the 2D gradient magnitude of image intensity defined by equation E3.

$$\|\nabla u\| = \sqrt{u_x^2 + u_y^2}, \quad \text{E3}$$

where
$u^2_x$=the square of the partial derivative of the pixel intensity (u) along the x-axis,
$u^2_y$=the square of the partial derivative of the pixel intensity (u) along the y-axis,
the Laplacian l(u) of the image, u, is expressed in equation E4 as $$l(u) = u_{xx}u_x^2 + 2u_{xy}u_xu_y + u_{yy}u_y^2 \quad \text{E4}$$

where equation E4 relates to equation E1 as follows:
$u_x$ is the first partial derivative $$\frac{\partial u}{\partial x}$$

of u along the x-axis,
$u_y$ is the first partial derivative $$\frac{\partial u}{\partial y}$$

of u along the y-axis,
$u_x^2$ is the square of the first partial derivative $$\frac{\partial u}{\partial x}$$

of u along the x-axis,
$u_y^2$ is the square of the first partial derivative $$\frac{\partial u}{\partial y}$$

of u along the y-axis,
$u_{xx}$ is the second partial derivative $$\frac{\partial^2 u}{\partial x^2}$$

of u along the x-axis,
$u_{yy}$ is the second partial derivative $$\frac{\partial^2 u}{\partial y^2}$$

of u along the y-axis,
$u_{xy}$ is cross multiple first partial derivative $$\frac{\partial u}{\partial x \partial y}$$

of u along the x and y axes, and
the sign of the function F modifies the Laplacian by the image gradient values selected to avoid placing spurious edges at points with small gradient values:

$$F(l(u)) = 1, \text{ if } l(u) > 0 \text{ and } \|\nabla u\| > t$$
$$= -1, \text{ if } l(u) < 0 \text{ and } \|\nabla u\| > t$$
$$= 0, \text{ otherwise}$$

where t is a threshold on the pixel gradient value $\|\nabla u\|$.

The combination of heat filtering and shock filtering produces an enhanced image ready to undergo the intensity-based and edge-based segmentation algorithms as discussed below.

FIG. 8B depicts the sub-algorithms of Intensity-Based Segmentation (step 422 in FIG. 7). The intensity-based segmentation step 422 uses a "k-means" intensity clustering 522 technique where the enhanced image is subjected to a categorizing "k-means" clustering algorithm. The "k-means" algorithm categorizes pixel intensities into white, gray, and black pixel groups. Given the number of desired clusters or groups of intensities (k), the k-means algorithm is an iterative algorithm comprising four steps:

1. Initially determine or categorize cluster boundaries by defining a minimum and a maximum pixel intensity value for every white, gray, or black pixels into groups or k-clusters that are equally spaced in the entire intensity range.

2. Assign each pixel to one of the white, gray or black k-clusters based on the currently set cluster boundaries.

3. Calculate a mean intensity for each pixel intensity k-cluster or group based on the current assignment of pixels into the different k-clusters. The calculated mean intensity is defined as a cluster center. Thereafter, new cluster boundaries are determined as mid points between cluster centers.

4. Determine if the cluster boundaries significantly change locations from their previous values. Should the cluster boundaries change significantly from their previous values, iterate back to step 2, until the cluster centers do not change significantly between iterations. Visually, the clustering process is manifest by the segmented image and repeated iterations continue until the segmented image does not change between the iterations.

The pixels in the cluster having the lowest intensity value—the darkest cluster—are defined as pixels associated with amniotic fluid. For the 2D algorithm, each image is clustered independently of the neighboring images. For the 3D algorithm, the entire volume is clustered together. To make this step faster, pixels are sampled at 2 or any multiple sampling rate factors before determining the cluster boundaries. The cluster boundaries determined from the down-sampled data are then applied to the entire data.

FIG. 8C depicts the sub-algorithms of Edge-Based Segmentation (step 438 in FIG. 7) and uses a sequence of four sub-algorithms. The sequence includes a spatial gradients 526 algorithm, a hysteresis threshold 530 algorithm, a Region-of-Interest (ROI) 534 algorithm, and a matching edges filter 538 algorithm.

The spatial gradient 526 computes the x-directional and y-directional spatial gradients of the enhanced image. The Hysteresis threshold 530 algorithm detects salient edges. Once the edges are detected, the regions defined by the edges are selected by a user employing the ROI 534 algorithm to select regions-of-interest deemed relevant for analysis.

Since the enhanced image has very sharp transitions, the edge points can be easily determined by taking x- and y-derivatives using backward differences along x- and y-directions. The pixel gradient magnitude $\|\nabla I\|$ is then computed from the x- and y-derivative image in equation E5 as:

$$\|\nabla I\| = \sqrt{I_x^2 + I_y^2} \qquad E5$$

Where $I^2_x$=the square of x-derivative of intensity; and
$I^2_y$=the square of y-derivative of intensity along the y-axis.

Significant edge points are then determined by thresholding the gradient magnitudes using a hysteresis thresholding operation. Other thresholding methods could also be used. In hysteresis thresholding 530, two threshold values, a lower threshold and a higher threshold, are used. First, the image is thresholded at the lower threshold value and a connected component labeling is carried out on the resulting image. Next, each connected edge component is preserved which has at least one edge pixel having a gradient magnitude greater than the upper threshold. This kind of thresholding scheme is good at retaining long connected edges that have one or more high gradient points.

In the preferred embodiment, the two thresholds are automatically estimated. The upper gradient threshold is estimated at a value such that at most 97% of the image pixels are marked as non-edges. The lower threshold is set at 50% of the value of the upper threshold. These percentages could be different in different implementations. Next, edge points that lie within a desired region-of-interest are selected 534. This region of interest selection 534 excludes points lying at the image boundaries and points lying too close to or too far from the transceiver 10. Finally, the matching edge filter 538 is applied to remove outlier edge points and fill in the area between the matching edge points.

The edge-matching algorithm 538 is applied to establish valid boundary edges and remove spurious edges while filling the regions between boundary edges. Edge points on an image have a directional component indicating the direction of the gradient. Pixels in scanlines crossing a boundary edge location will exhibit two gradient transitions depending on the pixel intensity directionality. Each gradient transition is given a positive or negative value depending on the pixel intensity directionality. For example, if the scanline approaches an echo reflective bright wall from a darker region, then an ascending transition is established as the pixel intensity gradient increases to a maximum value, i.e., as the transition ascends from a dark region to a bright region. The ascending transition is given a positive numerical value. Similarly, as the scanline recedes from the echo reflective wall, a descending transition is established as the pixel intensity gradient decreases to or approaches a minimum value. The descending transition is given a negative numerical value.

Valid boundary edges are those that exhibit ascending and descending pixel intensity gradients, or equivalently, exhibit paired or matched positive and negative numerical values. The valid boundary edges are retained in the image. Spurious or invalid boundary edges do not exhibit paired ascending-descending pixel intensity gradients, i.e., do not exhibit paired or matched positive and negative numerical values. The spurious boundary edges are removed from the image.

For amniotic fluid volume related applications, most edge points for amniotic fluid surround a dark, closed region, with directions pointing inwards towards the center of the region. Thus, for a convex-shaped region, the direction of a gradient for any edge point, the edge point having a gradient direction approximately opposite to the current point represents the matching edge point. Those edge points exhibiting an assigned positive and negative value are kept as valid edge points on the image because the negative value is paired with its positive value counterpart. Similarly, those edge point candidates having unmatched values, i.e., those edge point candidates not having a negative-positive value pair, are deemed not to be true or valid edge points and are discarded from the image.

The matching edge point algorithm 538 delineates edge points not lying on the boundary for removal from the desired dark regions. Thereafter, the region between any two matching edge points is filled in with non-zero pixels to establish edge-based segmentation. In a preferred embodiment of the invention, only edge points whose directions are primarily oriented co-linearly with the scanline are sought to permit the detection of matching front wall and back wall pairs.

Returning to FIG. 7, once Intensity-Based 422 and Edge-Based Segmentation 438 is completed, both segmentation methods use a combining step that combines the results of intensity-based segmentation 422 step and the edge-based segmentation 438 step using an AND Operator of Images 442. The AND Operator of Images 442 is achieved by a pixel-wise Boolean AND operator 442 step to produce a segmented image by computing the pixel intersection of two images. The Boolean AND operation 442 represents the pixels as binary numbers and the corresponding assignment of an assigned intersection value as a binary number 1 or 0 by the combination of any two pixels. For example, consider any two pixels, say $pixel_A$ and $pixel_B$, which can have a 1 or 0 as assigned values. If $pixel_A$'s value is 1, and $pixel_B$'s value is 1, the assigned intersection value of $pixel_A$ and $pixel_B$ is 1. If the binary value of $pixel_A$ and $pixel_B$ are both 0, or if either $pixel_A$ or $pixel_B$ is 0, then the assigned intersection value of $pixel_A$ and $pixel_B$ is 0. The Boolean AND operation 542 takes the binary any two digital images as input, and outputs a third image with the pixel values made equivalent to the intersection of the two input images.

Figure 8D:
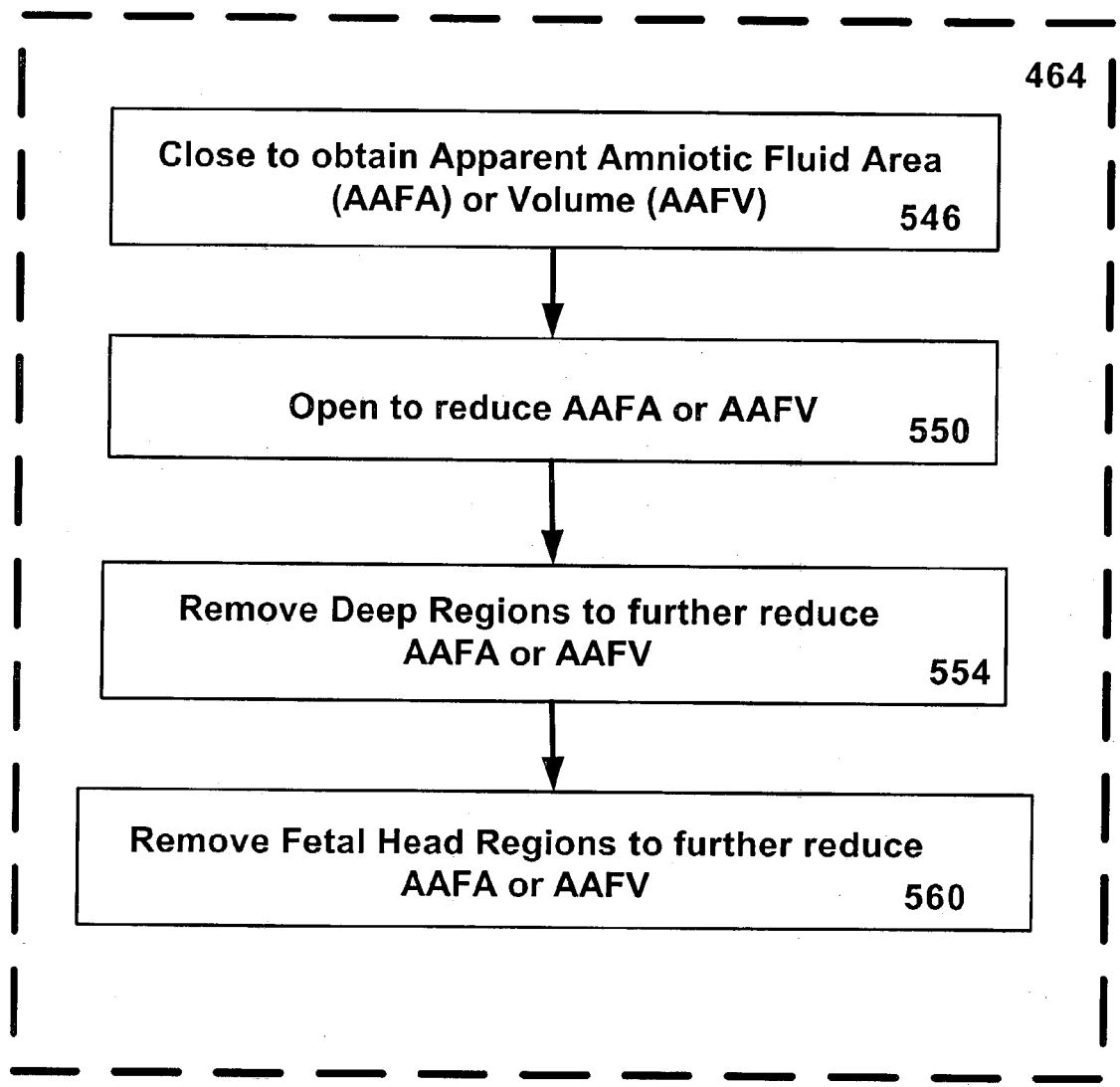
FIG. 8D depicts the sub-algorithms of the Polish algorithm, including Close, Open, Remove Deep Regions, and Remove Fetal Head Regions.

Upon completion of the AND Operator of Images 442 algorithm, the polish 464 algorithm of FIG. 7 is comprised of multiple sub-algorithms. FIG. 8D depicts the sub-algorithms of the Polish: 464 algorithm, including a Close 546 algorithm, an Open 550 algorithm, a Remove Deep Regions 554 algorithm, and a Remove Fetal Head Regions 560 algorithm.

Closing and opening algorithms are operations that process images based on the knowledge of the shape of objects contained on a black and white image, where white represents foreground regions and black represents background regions. Closing serves to remove background features on the image that are smaller than a specified size. Opening serves to remove foreground features on the image that are smaller than a specified size. The size of the features to be removed is specified as an input to these operations. The opening algorithm 550 removes unlikely amniotic fluid regions from the segmented image based on a-priori knowledge of the size and location of amniotic fluid pockets.

Referring to FIG. 8D, the closing 546 algorithm obtains the Apparent Anmiotic Fluid Area (AAFA) or Volume (AAFV) values. The AAFA and AAFV values are "Apparent" and maximal because these values may contain region areas or region volumes of non-amniotic origin unknowingly contributing to and obscuring what otherwise would be the true amniotic fluid volume. For example, the AAFA and AAFV values contain the true amniotic volumes, and possibly as well areas or volumes due to deep tissues and undetected fetal head volumes. Thus the apparent area and volume values require correction or adjustments due to unknown contributions of deep tissue and of the fetal head in order to determine an Adjusted Amniotic Fluid Area (AdAFA) value or Volume (AdAVA) value 568.

The AdAFA and AdAVA values obtained by the Close 546 algorithm are reduced by the morphological opening algorithm 550. Thereafter, the AdAFA and AdAVA values are further reduced by removing areas and volumes attributable to deep regions by using the Remove Deep Regions 554 algorithm. Thereafter, the polishing algorithm 464 continues by applying a fetal head region detection algorithm 560.

Figure 8E:
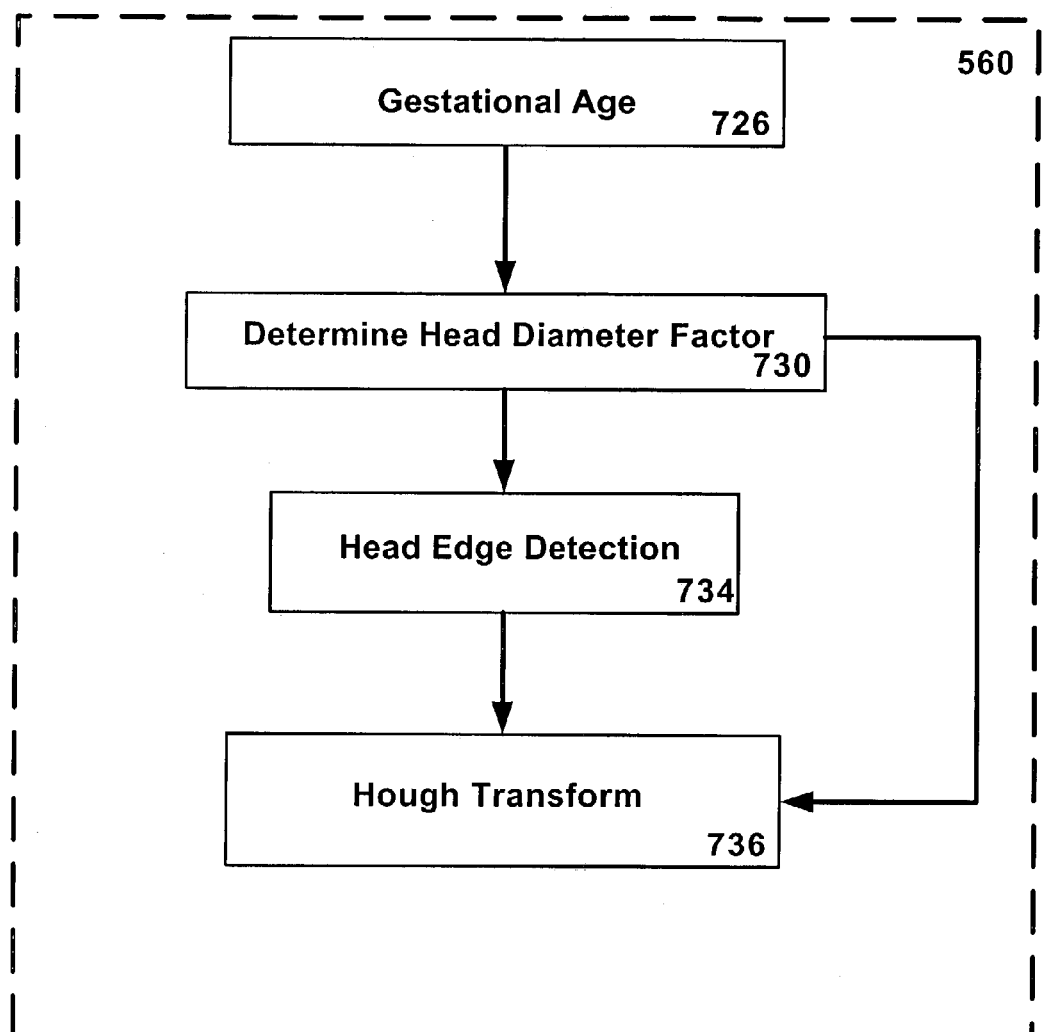
FIG. 8E depicts the sub-algorithms of the Remove Fetal Head Regions sub-algorithm.

FIG. 8E depicts the sub-algorithms of the Remove Fetal Head Regions sub-algorithm 560. The basic idea of the sub-algorithms of the fetal head detection algorithm 560 is that the edge points that potentially represent a fetal skull are detected. Thereafter, a circle finding algorithm to determine the best-fitting circle to these fetal skull edges is implemented. The radii of the circles that are searched are known a priori based on the fetus' gestational age. The best fitting circle whose fitting metric lies above a certain pre-specified threshold is marked as the fetal head and the region inside this circle is the fetal head region. The algorithms include a gestational Age 726 input, a determine head diameter factor 730 algorithm, a Head Edge Detection algorithm, 734, and a Hough transform procedure 736.

Fetal brain tissue has substantially similar ultrasound echo qualities as presented by amniotic fluid. If not detected and subtracted from amniotic fluid volumes, fetal brain tissue volumes will be measured as part of the total amniotic fluid volumes and lead to an overestimation and false diagnosis of oligo or poly-hyraminotic conditions. Thus detecting fetal head position, measuring fetal brain matter volumes, and deducting the fetal brain matter volumes from the amniotic fluid volumes to obtain a corrected amniotic fluid volume serves to establish accurately measure amniotic fluid volumes.

The gestational age input 726 begins the fetal head detection algorithm 560 and uses a head dimension table to obtain ranges of head bi-parietal diameters (BPD) to search for (e.g., 30 week gestational age corresponds to a 6 cm head diameter). The head diameter range is input to both the Head Edge Detection, 734, and the Hough Transform, 736., The head edge detection 734 algorithm seeks out the distinctively bright ultrasound echoes from the anterior and posterior walls of the fetal skull while the Hough Transform algorithm, 736, finds the fetal head using circular shapes as models for the fetal head in the Cartesian image (pre-scan conversion to polar form).

Scanplanes processed by steps 522, 538, 530, are input to the head edge detection step 734. Applied as the first step in the fetal head detection algorithm 734 is the detection of the potential head edges from among the edges found by the matching edge filter. The matching edge 538 filter outputs pairs of edge points potentially belonging to front walls or back walls. Not all of these walls correspond to fetal head locations. The edge points representing the fetal head are determined using the following heuristics:

(1) Looking along a one dimensional A-mode scan line, fetal head locations present a corresponding matching gradient in the opposing direction within a short distance approximately the same size as the thickness of the fetal skull. This distance is currently set to a value 1 cm.

(2) The front wall and the back wall locations of the fetal head are within a range of diameters corresponding to the expected diameter 730 for the gestational age 726 of the fetus. Walls that are too close or too far are not likely to be head locations.

(3) A majority of the pixels between the front and back wall locations of the fetal head lie within the minimum intensity cluster as defined by the output of the clustering algorithm 422. The percentage of pixels that need to be dark is currently defined to be 80%.

The pixels found satisfying these features are then vertically dilated to produce a set of thick fetal head edges as the output of Head Edge Detection, 734.

Figure 8F:
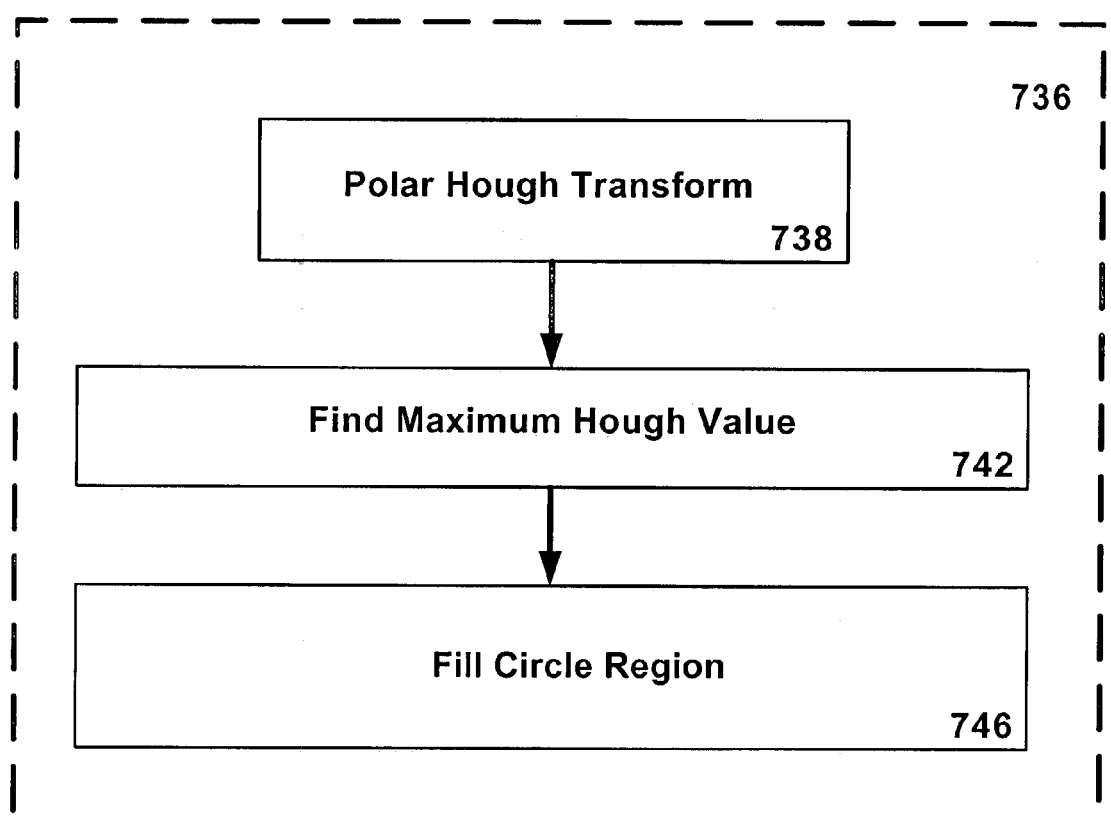
FIG. 8F depicts the sub-algorithms of the Hough Transform sub-algorithm.

FIG. 8F depicts the sub-algorithms of the Hough transform procedure 736. The sub-algorithms include a Polar Hough Transform 738 algorithm, a find maximum Hough value 742 algorithm 742, and a fill circle region 746. The Polar Hough Transform algorithm looks for fetal head structures in polar coordinate terms by converting from Cartesian coordinates using a plurality of equations. The fetal head, which appears like a circle in a 3D scan-converted Cartesian coordinate image, has a different shape in the pre-scan converted polar space. The fetal head shape is expressed in terms of polar coordinate terms explained as follows:

The coordinates of a circle in the Cartesian space (x,y) with center $(x_0, y_0)$ and radius R are defined for an angle $\theta$ are derived and defined in equation E5 as:

$$x = R \cos \theta + x_0$$

$$y = R \sin \theta + y_0$$

$$\Rightarrow (x-x_0)^2 + (y-y_0)^2 = R^2 \qquad \text{E5}$$

In polar space, the coordinates $(r, \phi)$, with respect to the center $(r_0, \phi_0)$, are derived and defined in equation E6 as:

$$r \sin \phi = R \cos \theta + r_0 \sin \phi_0$$

$$r \cos \phi = R \sin \theta + r_0 \cos \phi_0$$

$$\Rightarrow (r \sin \phi - r_0 \sin \phi_0)^2 + (r \cos \phi - r_0 \cos \phi_0)^2 = R^2 \qquad \text{E6}$$

The Hough transform 736 algorithm using equations E5 and E6 attempts to find the best-fit circle to the edges of an image. A circle in the polar space is defined by a set of three parameters, $(r_0, \phi_0, R)$ representing the center and the radius of the circle.

The basic idea for the Hough transform 736 is as follows. Suppose a circle is sought having a fixed radius (say, R1) for which the best center of the circle is similarly sought. Now, every edge point on the input image lies on a potential circle whose center lays R1 pixels away from it. The set of potential centers themselves form a circle of radius R1 around each edge pixel. Now, drawing potential circles of radius R1 around each edge pixel, the point at which most circles intersect, a center of the circle that represents a best-fit circle to the given edge points is obtained. Therefore, each pixel in the Hough transform output contains a likelihood value that is simply the count of the number of circles passing through that point.

Figure 9:
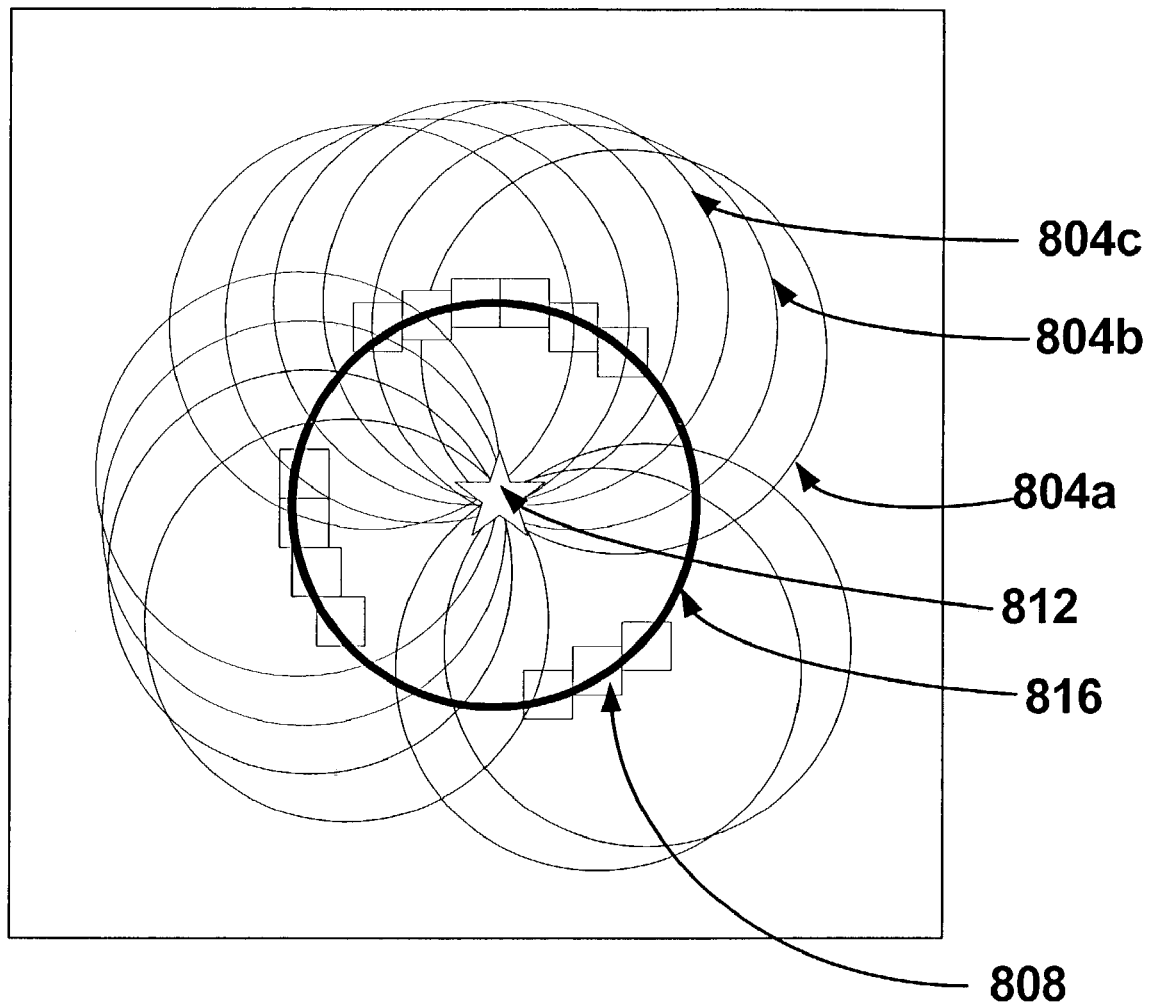
FIG. 9 depicts the operation of a circular Hough transform algorithm.

FIG. 9 illustrates the Hough Transform 736 algorithm for a plurality of circles with a fixed radius in a Cartesian coordinate system. A portion of the plurality of circles is represented by a first circle 804a, a second circle 804b, and a third circle 804c. A plurality of edge pixels are represented as gray squares and an edge pixel 808 is shown. A circle is drawn around each edge pixel to distinguish a center location 812 of a best-fit circle 816 passing through each edge pixel point; the point of the center location through which most such circles pass (shown by a gray star 812) is the center of the best-fit circle 816 presented as a thick dark line. The circumference of the best fit circle 816 passes substantially through is central portion of each edge pixel, represented as a series of squares substantially equivalent to the edge pixel 808.

This search for best fitting circles can be easily extended to circles with varying radii by adding one more degree of freedom—however, a discrete set of radii around the mean radii for a given gestational age makes the search significantly faster, as it is not necessary to search all possible radii.

The next step in the head detection algorithm is selecting or rejecting best-fit circles based on its likelihood, in the find maximum Hough Value 742 algorithm. The greater the number of circles passing through a given point in the Hough-space, the more likely it is to be the center of a best-fit circle. A 2D metric as a maximum Hough value 742 of the Hough transform 736 output is defined for every image in a dataset. The 3D metric is defined as the maximum of the 2D metrics for the entire 3D dataset. A fetal head is selected on an image depending on whether its 3D metric value exceeds a preset 3D threshold and also whether the 2D metric exceeds a preset 2D threshold. The 3D threshold is currently set at 7 and the 2D threshold is currently set at 5. These thresholds have been determined by extensive training on images where the fetal head was known to be present or absent.

Thereafter, the fetal head detection algorithm concludes with a fill circle region 746 that incorporates pixels to the image within the detected circle. The fill circle region 746 algorithm fills the inside of the best fitting polar circle. Accordingly, the fill circle region 746 algorithm encloses and defines the area of the fetal brain tissue, permitting the area and volume to be calculated and deducted via algorithm 554 from the apparent amniotic fluid area and volume (AAFA or AAFV) to obtain a computation of the corrected amniotic fluid area or volume via algorithm 484.

Figure 10:
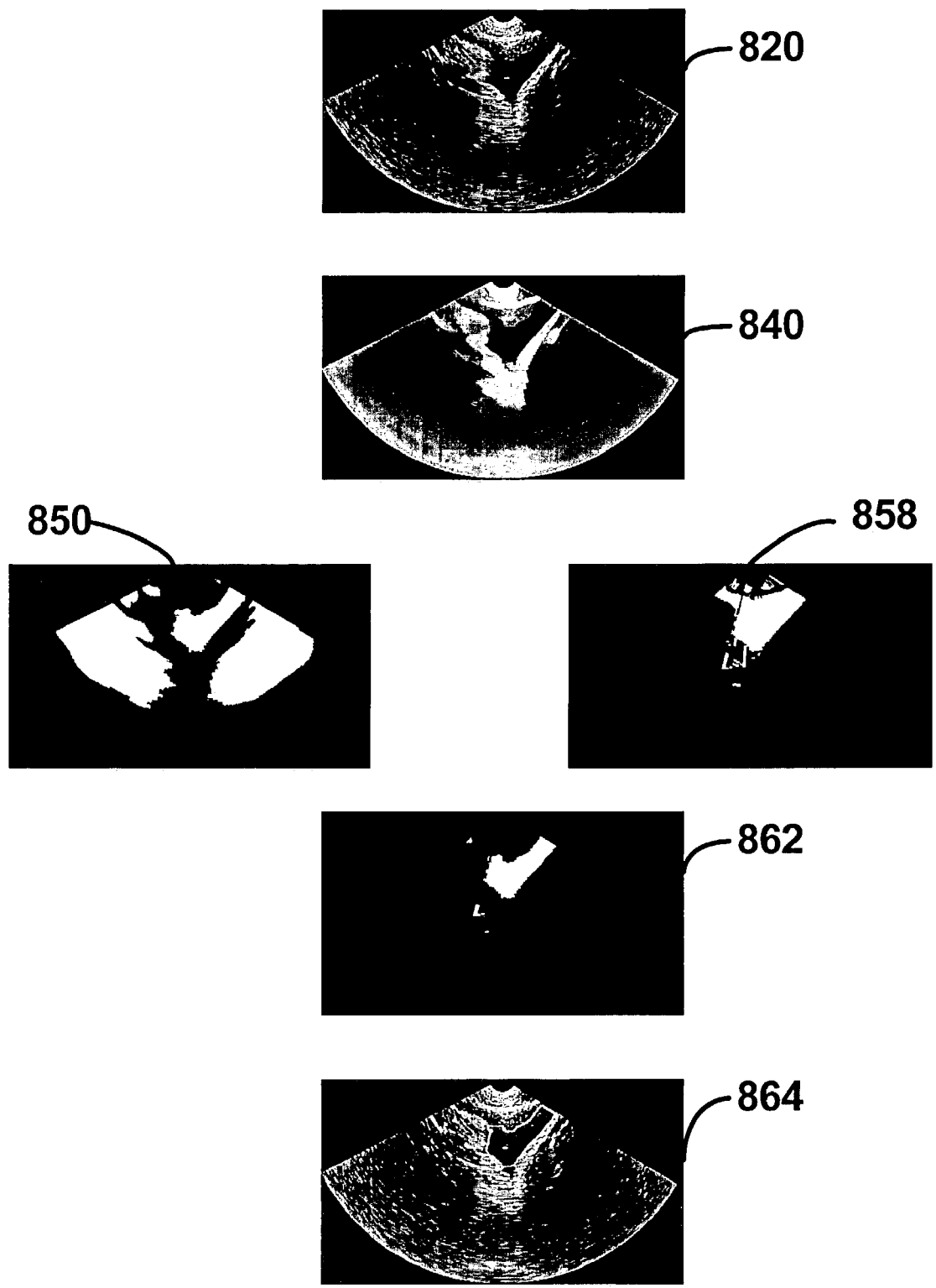
FIG. 10 shows results of sequentially applying the algorithm steps on a sample image.

FIG. 10 shows the results of sequentially applying the algorithm steps of FIGS. 7 and 8A–D on an unprocessed sample image 820 presented within the confines of a scanplane substantially equivalent to the scanplane 210. The results of applying the heat filter 514 and shock filter 518 in enhancing the unprocessed sample is shown in enhanced image 840. The result of intensity-based segmentation algorithms 522 is shown in image 850. The results of edge-based segmentation 438 algorithm using sub-algorithms 526, 530, 534 and 538 of the enhanced image 840 is shown in segmented image 858. The result of the combination 442 utilizing the Boolean AND images 442 algorithm is shown in image 862 where white represents the amniotic fluid area. The result of applying the polishing 464 algorithm employing algorithms 542, 546, 550, 554, 560, and 564 is shown in image 864, which depicts the amniotic fluid area overlaid on the unprocessed sample image 810.

Figure 11:
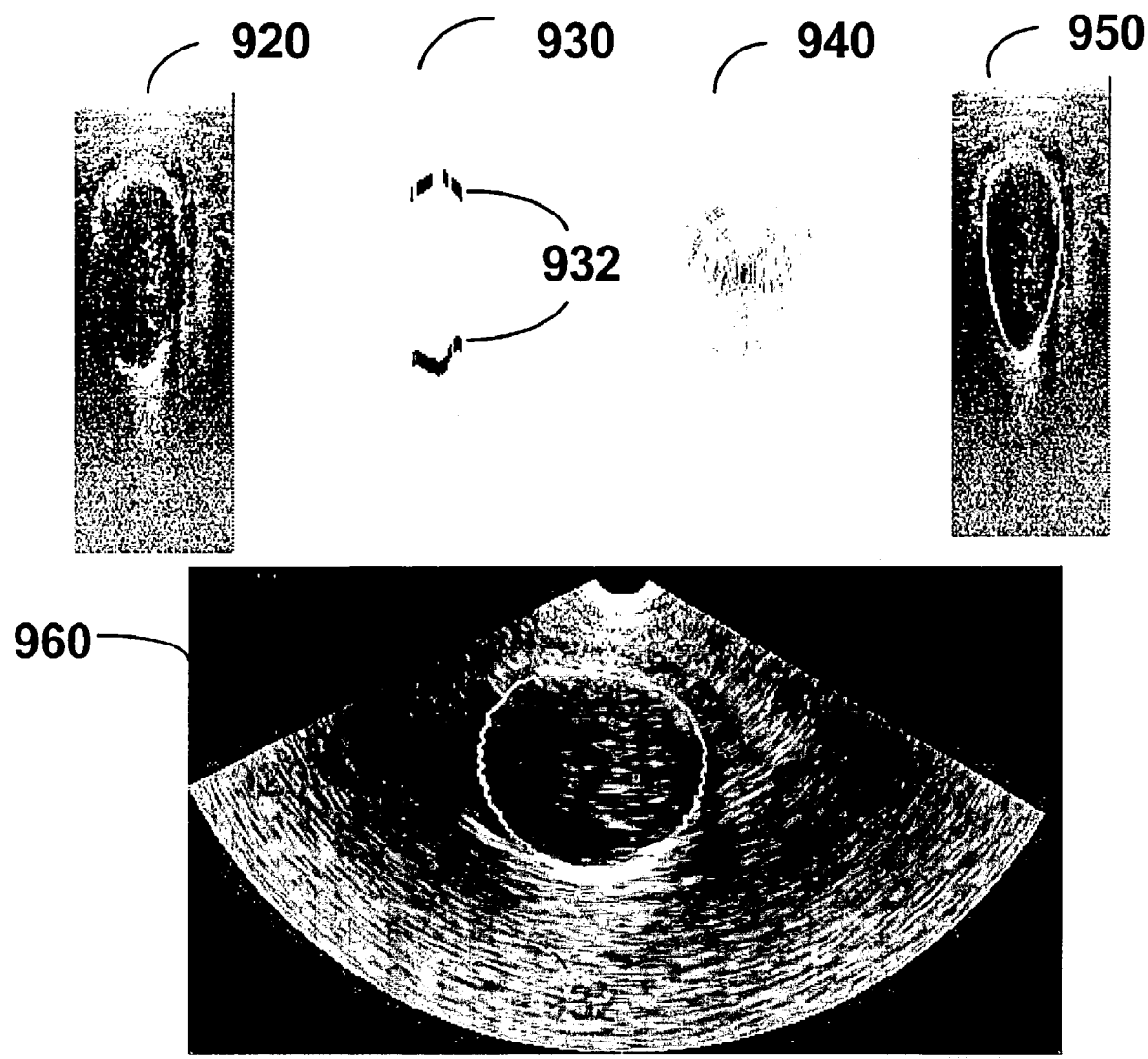
FIG. 11 illustrates a set of intermediate images of the fetal head detection process.

FIG. 11 depicts a series of images showing the results of the above method to automatically detect, locate, and measure the area and volume of a fetal head using the algorithms outlined in FIGS. 7 and 8A–F. Beginning with an input image in polar coordinate form 920, the fetal head image is marked by distinctive bright echoes from the anterior and posterior walls of the fetal skull and a circular shape of the fetal head in the Cartesian image. The fetal head detection algorithm 734 operates on the polar coordinate data (i.e., pre-scan version, not yet converted to Cartesian coordinates).

An example output of applying the head edge detection 734 algorithm to detect potential head edges is shown in image 930. Occupying the space between the anterior and posterior walls are dilated black pixels 932 (stacks or short lines of black pixels representing thick edges). An example of the polar Hough transform 738 for one actual data sample for a specific radius is shown in polar coordinate image 940.

An example of the best-fit circle on real data polar data is shown in polar coordinate image 950 that has undergone the find maximum Hough value step 742. The polar coordinate image 950 is scan-converted to a Cartesian data in image 960 where the effects of finding maximum Hough value 742 algorithm are seen in Cartesian format.

FIG. 12 presents a 4-panel series of sonographer amniotic fluid pocket outlines compared to the algorithm's output in a scanplane equivalent to scanplane 210. The top two panels depict the sonographer's outlines of amniotic fluid pockets obtained by manual interactions with the display while the bottom two panels show the resulting amniotic fluid boundaries obtained from the instant invention's automatic application of 2D algorithms, 3D algorithms, combination heat and shock filter algorithms, and segmentation algorithms.

After the contours on all the images have been delineated, the volume of the segmented structure is computed. Two specific techniques for doing so are disclosed in detail in U.S. Pat. No. 5,235,985 to McMorrow et al, herein incorporated by reference. This patent provides detailed explanations for non-invasively transmitting, receiving and processing ultrasound for calculating volumes of anatomical structures.

Demonstrations of the algorithmic manipulation of pixels of the present invention are provided in Appendix 1: Examples of Algorithmic Steps. Source code of the algorithms of the present invention is provided in Appendix 2: Matlab Source Code.

While the preferred embodiment of the invention has been illustrated and described, as noted above, many changes can be made without departing from the spirit and scope of the invention. For example, other uses of the invention include determining the areas and volumes of the prostate, heart, bladder, and other organs and body regions of clinical interest. Accordingly, the scope of the invention is not limited by the disclosure of the preferred embodiment.

We claim:

1. A method to determine amniotic fluid volume in digital images, the method comprising:

positioning an ultrasound transceiver exterior to a patient such that at least a portion of the amniotic fluid is within a field of view of the transceiver, the ultrasound transceiver configured to send radio frequency ultrasound pulses and to receive echoes of the radio frequency ultrasound pulses;

sending the radio frequency ultrasound pulses from the ultrasound transceiver to amniotic fluid regions;

receiving echoes of the radio frequency ultrasound pulses reflected from the amniotic fluid regions to the transceiver;

associating the received echoes to form a plurality of 2D scanplanes so that they form an array;

enhancing the images of the amniotic fluid regions in each plane of the array using a plurality of algorithms; and determining the amniotic fluid volume of the amniotic fluid regions spanning between and through each plane in the array.

2. The method of claim 1, wherein plurality of 2D scanplanes are acquired from a rotational array, a translational array, or a wedge array.

3. The method of claim 1, wherein the plurality of 2D scanplanes includes at least two scanplanes.

4. The method of claim 1, wherein the radio frequency ultrasound is within a range from approximately 2 MHz to approximately 10 MHz.

5. The method of claim 1, wherein the plurality of algorithms includes algorithms for image enhancement, segmentation, and polishing.

6. The method of claim 5, wherein segmentation further includes an intensity clustering step, a spatial gradients step, a hysteresis threshold step, a Region-of-Interest selection step, and a matching edges filter step.

7. The method of claim 6, wherein the intensity clustering step is performed in a first parallel operation, and the spatial gradients, hysteresis threshold, Region-of-Interest selection, and matching edges filter steps are performed in a second parallel operation, and further wherein the results from the first parallel operation are combined with the results from the second parallel operation.

8. The method of claim 1, wherein image enhancement further includes applying a heat filter and a shock filter to the digital images.

9. The method of claim 8 wherein the heat filter is applied to the digital images followed by application of the shock filter to the digital images.

10. The method of claim 9, wherein the heat filter is a partial differential equation of an inputted image pixel intensity u expressed in an equation defined as $$\frac{\partial u}{\partial t} = \frac{\partial^2 u}{\partial x^2} + \frac{\partial^2 u}{\partial y^2},$$

where u is the image being processed, $$\frac{\partial^2 u}{\partial x^2}$$

is the second partial derivative of u along the x-axis, and $$\frac{\partial^2 u}{\partial y^2}$$

is the second partial derivative of u along the y-axis.

11. The method of claim 8, wherein the shock filter is a partial differential equation of an imputed image pixel intensity u expressed in an equation defined as $$\frac{\partial u}{\partial t} = -F(l(u))\|\nabla u\|,$$

where u is the image being processed, l(u) is the Laplacian of the image u, F is a function of the Laplacian, and $\|\nabla u\|$ is the 2D gradient magnitude of image intensity equivalent to $$\sqrt{u_x^2 + u_y^2},$$

where $u^2_x$=the square of pixel intensity along the x-axis, and $u^2_y$=the square of pixel intensity along the y-axis.

12. The method of claim 1 wherein the amniotic fluid volume is adjusted for underestimation or overestimation.

13. The method of claim 12, wherein the amniotic fluid volume is adjusted for underestimation by probing with adjustable ultrasound frequencies to penetrate deep tissues and to repositioning the transceiver to establish that deep tissues are exposed with probing ultrasound of sufficient strength to provide a reflecting ultrasound echo receivable by the transceiver, such that more than one rotational array to detect deep tissue and regions of the fetal head are obtained.

14. The method of claim 12, wherein amniotic fluid volume is adjusted for overestimation by automatically determining fetal head volume contribution to amniotic fluid volume and deducting it from the amniotic fluid volume.

15. The method of claim 14, wherein the steps to adjust for overestimated amniotic fluid volumes include a 2D clustering step, a matching edges step, an all edges step, a gestational age factor step, a head diameter step, an head edge detection step, and a Hough transform step.

16. The method of claim 15, wherein the Hough transform step includes a polar Hough Transform step, a Find Maximum Hough value step, and a fill circle region step.

17. The method of claim 16, wherein the polar Hough Transform step includes a first Flough transform to look for lines of a specified shape, and a second Hough transform to look for fetal head structures.

18. A system for determining amniotic fluid volume, the system comprising:

a transceiver configured to deliver radio frequency ultrasound pulses to amniotic fluid regions of a patient, to receive echoes of the pulses reflected from the amniotic fluid regions, and to convert the echoes to digital form;

a computer system in communication with the transceiver, the computer system having a microprocessor and a memory, the memory further containing stored programming instructions operable by the microprocessor to associate a plurality of scanplanes into a rotational array; and the memory further containing instructions operable by the microprocessor to determine the presence of an amniotic fluid region in each scanplane and determine the amniotic fluid volume spanning between and through each scanplane of the rotational array.

19. The system of claim 18, wherein the radio frequency pulses are in a range of approximately 2 MHz to approximately 10 MHz.

20. The system of claim 18, wherein each scanplane is arranged as a plurality of scanlines, each scanline of the plurality of scanlines being separated by approximately 1.5 degrees and having a length suitable for the dimension of amniotic fluid region.

21. The system of claim 18, wherein each scanplane in the plurality of scanplanes is separated from an adjacent scanplane in the plurality of scanplanes by approximately 7.5 degrees.

22. The system of claim 18, wherein the transceiver includes a display to present the graphic image of a scanplane in two-dimensions and the rotational array in three-dimensions.

23. The system of claim 18, wherein the plurality of algorithms includes steps for image enhancement, segmentation, and polishing.

24. The system of claim 23, wherein the steps for image enhancement further include application of a heat filter followed by application of a shock filter.

25. The system of claim 18, wherein the amniotic fluid volumes are adjusted for underestimation and overestimation.

26. The system of claim 25, wherein the amniotic fluid volumes are adjusted for underestimation by probing with ultrasound frequencies having sufficient power and wavelength to penetrate through fatty tissue to reach amniotic fluid regions and to provide detectable echo signals receivable to the transceiver to reveal amniotic fluid regions.

27. The system of claim 26, wherein the amniotic fluid volumes are further adjusted for underestimation by repositioning the transceiver to acquire more than one rotational array to detect deep tissue and regions of the fetal head.

28. The system of claim 25, wherein the amniotic fluid volumes are adjusted for overestimation by detecting the location of a fetal head, determining the volume of the fetal head, and deducting the volume of the fetal head from the amniotic fluid volume spanning between and through each scanplane of the rotational array.

29. The system of claim 18, wherein the computer system is configured for remote operation via an Internet web-based system, the internet web-based system having a plurality of programs that collect, analyze, and store amniotic fluid volume.

30. A system for determining amniotic fluid volume, the system comprising:

a transceiver configured to deliver radio frequency ultrasound pulses in a range of approximately 2 MHz to approximately 10 MHz in a plurality of scanplanes to amniotic fluid regions of a patient, to receive echoes of the pulses reflected from the anmiotic fluid regions, and to convert the echoes to digital signals;

a computer system in communication with the transceiver, the computer system having a microprocessor and a memory, the memory further containing stored programming instructions operable by the microprocessor to associate the plurality of scanplanes into a rotational array; and a plurality of algorithms operable by the microprocessor to determine the presence of an amniotic fluid region in each scanplane and determine the amniotic fluid volume spanning between and through each scanplane of the rotational array.

31. The system of claim 30, wherein the amniotic fluid volumes are adjusted for underestimation by repositioning the transceiver to acquire more than one rotational array to detect deep tissue and regions of the fetal head.

32. The system of claim 30, wherein the amniotic fluid volumes are adjusted for overestimation by detecting the location of a fetal head, determining the volume of the fetal head, and deducting the volume of the fetal head from the amniotic fluid volume spanning between and through each scanplane of the rotational array.

33. The system of claim 32, wherein the location of the fetal head is determined by a Hough transform, the Hough transform including a The method of claim 16, wherein the Hough transform step includes a polar Hough Transform step, a Find Maximum Hough value step, and a fill circle region step.

34. The method of claim 33, wherein the polar Hough Transform step includes a standard Hough transform to look for lines of a specified shape, and a modified Hough transform to look for fetal head structures.

* * * * *